(12) United States Patent
Elhawary et al.

(10) Patent No.: US 10,674,965 B2
(45) Date of Patent: Jun. 9, 2020

(54) SYSTEM AND METHOD FOR MONITORING SAFETY AND PRODUCTIVITY OF PHYSICAL TASKS

(71) Applicant: One Million Metrics Corp., New York, NY (US)

(72) Inventors: Haytham Elhawary, New York, NY (US); Aditya Bansal, White Plains, NY (US); Firdaus Janoos, Jersey City, NJ (US); Selim Youssry, New York, NY (US); Enrique Ruiz de Villa, Santander (ES)

(73) Assignee: ONE MILLION METRICS CORP., New York, NY (US)

( * ) Notice: Subject to any disclaimer, the term of this patent is extended or adjusted under 35 U.S.C. 154(b) by 383 days.

(21) Appl. No.: 15/594,177

(22) Filed: May 12, 2017

(65) Prior Publication Data
US 2017/0245806 A1    Aug. 31, 2017

Related U.S. Application Data

(63) Continuation of application No. 14/660,578, filed on Mar. 17, 2015, now Pat. No. 9,833,197.
(Continued)

(51) Int. Cl.
*A61B 5/00* (2006.01)
*A61B 5/11* (2006.01)
(Continued)

(52) U.S. Cl.
CPC .......... *A61B 5/7275* (2013.01); *A61B 5/0022* (2013.01); *A61B 5/1116* (2013.01); *A61B 5/1118* (2013.01); *A61B 5/1121* (2013.01); *A61B 5/1122* (2013.01); *A61B 5/681* (2013.01); *A61B 5/6823* (2013.01); *A61B 5/6824* (2013.01); *A61B 5/6838* (2013.01); *G06F 19/3481* (2013.01); *G16H 20/30* (2018.01); *A61B 5/0024* (2013.01);
(Continued)

(58) Field of Classification Search
CPC ..... A61B 5/116; A61B 5/1121; A61B 5/1123; A61B 5/0022; A61B 5/7275; G16H 20/30
See application file for complete search history.

(56) References Cited

U.S. PATENT DOCUMENTS

| 7,457,678 B2 | 11/2008 | Smith et al. |
| 7,698,830 B2 | 4/2010 | Townsend et al. |

(Continued)

OTHER PUBLICATIONS

International Search Report with Written Opinion issued for corresponding International Application No. PCT/US2016/016062 dated May 26, 2016, pp. 1-6.
(Continued)

*Primary Examiner* — Max F Hindenburg
(74) *Attorney, Agent, or Firm* — Myers Wolin, LLC

(57) ABSTRACT

Methods and systems for monitoring workplace safety and evaluating risks is provided, the method comprising receiving signals from at least one wearable device, identifying portions of the signals corresponding to physical activities, excerpting the portions of the signals corresponding to the physical activities, and calculating risk metrics based on measurements extracted from the excerpted portions of the signals, the risk metric indicative of high risk lifting activities.

23 Claims, 16 Drawing Sheets

Related U.S. Application Data

(60) Provisional application No. 61/953,934, filed on Mar. 17, 2014, provisional application No. 62/110,630, filed on Feb. 2, 2015, provisional application No. 62/335,070, filed on May 12, 2016.

(51) Int. Cl.
*G06F 19/00* (2018.01)
*G16H 20/30* (2018.01)
*G16H 50/30* (2018.01)

(52) U.S. Cl.
CPC .......... *A61B 5/7405* (2013.01); *A61B 5/7475* (2013.01); *A61B 2503/20* (2013.01); *A61B 2560/0223* (2013.01); *A61B 2562/0219* (2013.01); *G16H 50/30* (2018.01)

(56) References Cited

U.S. PATENT DOCUMENTS

| | | |
|---|---|---|
| 7,797,771 B1 | 9/2010 | Bossen et al. |
| 8,149,126 B2 | 4/2012 | Little et al. |
| 8,638,228 B2 | 1/2014 | Amigo et al. |
| 8,712,827 B2 | 4/2014 | Mollicone et al. |
| 8,942,662 B2 | 1/2015 | Pan et al. |
| 9,566,441 B2 * | 2/2017 | Skelton ............ A61N 1/36514 |
| 9,833,197 B1 * | 12/2017 | Elhawary ............... G16H 20/30 |
| 2007/0250286 A1 | 10/2007 | Duncan et al. |
| 2009/0135009 A1 | 5/2009 | Little et al. |
| 2011/0183305 A1 | 7/2011 | Orbach |
| 2011/0213278 A1 | 9/2011 | Horak et al. |
| 2012/0083676 A1 | 4/2012 | Wolfberg et al. |
| 2013/0103416 A1 | 4/2013 | Amigo et al. |
| 2013/0217352 A1 | 8/2013 | Pan et al. |
| 2013/0244211 A1 | 9/2013 | Dowling et al. |
| 2013/0331993 A1 | 12/2013 | Detsch et al. |
| 2013/0332098 A1 | 12/2013 | Funk et al. |
| 2014/0128778 A1 * | 5/2014 | Chan ..................... A61B 5/1116 600/595 |
| 2014/0135592 A1 | 5/2014 | Ohnemus et al. |
| 2014/0163337 A1 | 6/2014 | Horseman |
| 2014/0266160 A1 * | 9/2014 | Coza ..................... G01B 7/003 324/207.11 |
| 2014/0266737 A1 | 9/2014 | Caldwell |
| 2014/0317135 A1 | 10/2014 | Stivoric et al. |
| 2014/0347265 A1 | 11/2014 | Aimone et al. |

OTHER PUBLICATIONS

Anonymous: "Kinetic Introduces Wearables Against Lifting Injuries Using Intel Technology", Dec. 14, 2015. URL:https://www.prweb.com/pdfdlownload/13128927.pdf, retrieved from the internet on Aug. 27, 2018.

Klint: "The Internet of Anything: This Wearable Could Keep You From Throwing Out Your Back", Feb. 23, 2015 URL:https://wired.com/2015/02/kinetic-wearable-back-protection/, retrieved from the internet on Aug. 27, 2018.

Kinetic: "Kinetic description—We're building wearable devices to improve industrial worker safety", Feb. 11, 2015 URL:https://www.youtube.com/watch?v=AdrZTg9sU_E, retrieved from the Internet on Aug. 27, 2018.

Extend European search report with the European search opinion issued for corresponding European Patent Application No. 16747074.9 dated Sep. 6, 2018.

The extended European search report with supplementary European search report and the European search opinion issued by the European Patent Office for corresponding European Patent Application No. 17796966.4, dated Nov. 27, 2019.

* cited by examiner

SYSTEM AND METHOD FOR MONITORING SAFETY AND PRODUCTIVITY OF PHYSICAL TASKS

CROSS-REFERENCE TO RELATED APPLICATION

This application claims the benefit of U.S. Provisional Patent Application No. 62/335,070, filed May 12, 2016, and is a continuation of U.S. patent application Ser. No. 14/660,578, filed Mar. 17, 2015 which claims the benefit of U.S. Provisional Patent Application No. 61/953,934, filed Mar. 17, 2014, and U.S. Provisional Patent Application No. 62/110,630, filed Feb. 2, 2015, the contents of each of which are incorporated by reference herein in its entirety.

FIELD OF THE INVENTION

The system and method relate to monitoring workplace safety and productivity and generating recommendations to improve such safety and productivity.

BACKGROUND

In industries that require physical manipulation of objects or people, such as material handling, patient handling, manufacturing, or construction, workers often perform a variety of manual tasks such as lifting loads, moving loads from one location to another, pushing and pulling carts or trolleys, complex assembly and manipulation of components using specific motions and using vibration and impact tools. Often these motions require an intense physical effort, and therefore the repetition of these tasks over time can cause fatigue and injury.

Wearable technology has been used extensively in the consumer space to quantify, for example, the number of steps taken, distance traveled, length and quality of sleep and other metrics, but wearable technology has not been able to consistently evaluate safety metrics in the materials handling industry.

Many risks associated with material handling workers exist, including repetitive stress injuries based on extended physical effort over prolonged periods of time.

Current solutions are mostly limited to physical inspection by specialists, since there is a lack of effective tools to predict when lifting posture is incorrect, or when fatigue results in a risky or dangerous change of posture or non-ergonomic lifting techniques when performing tasks. Typically, specialists inspect the workplace and observe tasks, or review video footage provided by the employer. In either case, inspection is typically performed over only a limited period of time, usually 5-60 minutes. Without effective tools, employers (and workers themselves) have difficulty predicting and preventing injury.

Further, while workers are taught correct material handling techniques, such techniques are not tailored to the strengths of a particular worker. Different workers can do a particular task in multiple ways because of varying body types and abilities. Better monitoring of task performance incorporating information about the particular worker involved may allow for customized training techniques.

Further, there is a lack of productivity measuring tools for individual workers, as it is rarely possible to measure in real-time the number and quality of tasks a specific worker is performing including their speed and variation over time. This information could allow managers to optimize productivity or to devise novel forms of incentives based on productivity.

Finally, tasks are typically divided among the workers based partially on physical ability. However, the physical ability to do a specific task is determined based on visual observation without any detailed insights on the actual motion of a worker's body. Quantifying body motion can help supervisors factor such information into task and shift assignments. Therefore, additional information related to the aspects of task performance that increase injury risk can inform the design of a workplace, design of shifts, and assignment of tasks.

Existing systems for analyzing the safety and productivity of material handling tasks by analyzing motion have limited real-world applications due to inherent limitations.

Motion detection based platforms, such as optical systems using complex cameras and sensors, are expensive and are of limited use in a warehouse setting as they require line of sight which is not always possible in crowded warehouse or factory environments.

Electromagnetic based motion sensor systems produce errors when they are close to ferromagnetic materials often present in industrial settings, are expensive and typically require cabling from sensors to processing units, making their continued use impractical in a warehouse setting.

Existing devices provide very limited motion information and are typically bulky and impractical. Existing systems cannot extract adequate information to fully implement risk models, and typically require manual input of risk variables that cannot be measured by the device alone.

There is a need for a fully automatable system and method that can monitor physical activity of individual workers and evaluate safety and productivity both for individuals and for a workspace as a whole. There is a further need for a platform that can incorporate such evaluations into recommendations for improving the technique of individual workers and physical characteristics of the workplace environment.

SUMMARY

A computer-based method for identifying risk during lifting activities is provided, wherein a computing device receives a first signal from a wearable device indicative of physical characteristics of the device over time. In some embodiments, the computing device separately receives a second signal from a wearable second device. The computing device identifies, from the first signal and/or the second signal, an initiation time for a physical activity, such as a lifting activity performed by a wearer of the first device and the second device. The computing device then identifies a signal segment from the first signal for a time period corresponding to an initiation of a physical activity.

The computing device then calculates measurements of the wearer for the time period during the lifting activity from the first signal segment and the second signal segment and calculates a risk metric from a risk model based on the measurements of the wearer for the time period during the lifting activity, the risk metric being indicative of high risk lifting activity.

In some embodiments, the measurement of the wearer include measurements of a user's back inferred from movement of the user's hip detected by a wearable device at the user's hip. In such an embodiment, the movement of the user's hip may be detected by an accelerometer, a gyroscope, and an altimeter.

In some embodiments, the physical activity is not a lifting activity, but is instead, a user jumping off of a raised surface, such as the back of a truck, or a user falling.

The computing device may also determine a conclusion time for the lifting activity and may perform the method continuously over the course of an evaluation period in order to evaluate multiple lifting activities. Such a platform may calculate a cumulative risk metric, and may generate feedback to a worker wearing the devices when the cumulative risk metric indicates high risk.

The computing device may further provide calibration methods for comparing an orientation of the wearable device to an expected orientation in order to properly calibrate the device prior to or during the detection of physical activity.

The computing device may also determine a physical location or a physical activity, such as a lifting activity, corresponding to individual lifting activities, such that risk metrics may be correlated with locations or activities. Similarly, the computing device may then provide recommendations related to the particular location or activity corresponding to an increased value of the risk metric. For example, such a platform may recommend avoiding lifts beginning near the floor of the warehouse in a specific location within the warehouse.

Measurements extracted from the signals may correspond to a horizontal location of a first device relative to a second device, a vertical location of the first device relative to a floor at the initiation time of the lifting activity, a vertical location of the first device relative to the floor following the lifting activity, a rotation angle of the first device or the second device, indicating rotation of the worker's trunk, a frequency of lifting activities during the evaluation period, and a duration of the evaluation period. These values may be used to determine a risk metric in the form of a maximum weight of a package that should not be exceeded, for example.

Additional metrics may be calculated as well, such as productivity metrics, and in some embodiments, the data provided by the devices may be used to, for example, estimate the weight of a package being lifted based on angular velocity of a sensor mounted on a workers wrist.

The wearable devices described may be further networked with other devices to provide additional safety features, such as the confirmation of proper use of safety equipment and the like.

In some embodiments, a method is provided for calibrating a wearable device comprising determining that an actual physical posture of a user wearing the wearable device corresponds to a known physical posture, receiving a first signal from the wearable device generated from dynamic activity of the wearable device over time, and initiating a calibration sequence including excerpting a calibration window of the first signal and recording offsets in the first signal relative to physical characteristics corresponding to the known physical posture.

The confirming that an actual physical posture corresponds to a known physical posture may be by providing the user with a wearable device, monitoring a clip of the wearable device, and confirming closure of the clip. The closure of the clip may be registered with a magnetic field sensor. Alternatively, the confirming may be by the user indicating that he is in a predetermined physical posture, or by instructing the user to conform to an initial posture and indicate the assumption of that initial posture.

Such an embodiment further comprises incorporating the offset into an adjusted first signal, and identifying a signal segment corresponding to a physical activity in the adjusted first signal and identifying the physical activity based on the signal segment. Thy physical activity may be a lifting activity performed by the user, and the method may then calculate a risk metric from a risk model based on the signal segment, the risk metric being indicative of a high risk physical activity.

In some embodiments, the signal segment is identified by identifying an initiation time for the lifting activity and excerpting the signal segment corresponding to a time period after the initiation time. The method may further determine a conclusion time for the lifting activity and repeat the method to identify a plurality of lifting activities over an evaluation period.

In some embodiments, the method continues to monitor the first signal for known categories of calibration errors. This may be by identifying, in the adjusted first signal, a signal segment corresponding to a known category of calibration error, such as a single segment corresponding to a rotated device. The method then identifies a known activity, such as a user walking, and initiates the calibration sequence.

The method may further identify, in a calibration signal segment corresponding to an expected pattern for a calibration activity, a device location relative to the user based on a variance between the calibration signal segment and an expected pattern. For example, the method may identify that the device location is a side of the body or a height relative to the user's hips.

In some embodiments, a method may be provided for enforcing safety rules by receiving a first signal from a wearable device indicative of dynamic activity of the device, identifying a signal segment corresponding to one of several expected activities, and determining that the physical activity to which the segment corresponds requires a specified item of safety equipment, such as a harness or a hardhat, determining the presence of that safety equipment, and triggering an alert if the safety equipment is absent. In some embodiments, the presence of the safety equipment and the proper use or installation of the safety equipment is confirmed by a received signal.

In some embodiments, the method identifies the presence of a piece of industrial activity, and selects the expected physical activities, as well as the required safety equipment, based on the piece of industrial equipment.

In some embodiments, the method further comprises identifying the expected physical activities based on the identity of the user or a location or altitude of the user.

In some embodiments, the wearable device transmits an activation key for a piece of equipment, and the piece of equipment requires safety equipment or safety certification for use. In such an embodiment, the wearable device may transmit the activation key only upon confirming the presence of the safety equipment or certification.

In some embodiments, a system may be provided for ensuring the safety of workers in an environment comprising a first wearable device having a first and second communication interface, a plurality of secondary devices each containing an environmental sensor and a transmitter for transmitting a wireless signal containing environmental data, a server, and a database associated with the server.

In such an embodiment, the wearable device may receive the wireless signal of one of secondary sensors at the first communication interface and may transmit a secondary wireless signal comprising the environmental data, such as temperature, humidity, or gas level, at the second wireless interface to either the server or a second wearable device. The server then records the data with the identification of the secondary device in a database and monitors for unexpected changes in the environmental data.

In some embodiments, the method may further comprise recording several physical activities in a log of physical activities. The identification of such physical activities may be assisted by data related to the location of the wearable device, an expected schedule for a user, or the presence of nearby wearable devices or equipment.

DETAILED DESCRIPTION OF THE PREFERRED EMBODIMENTS

Figure 1:
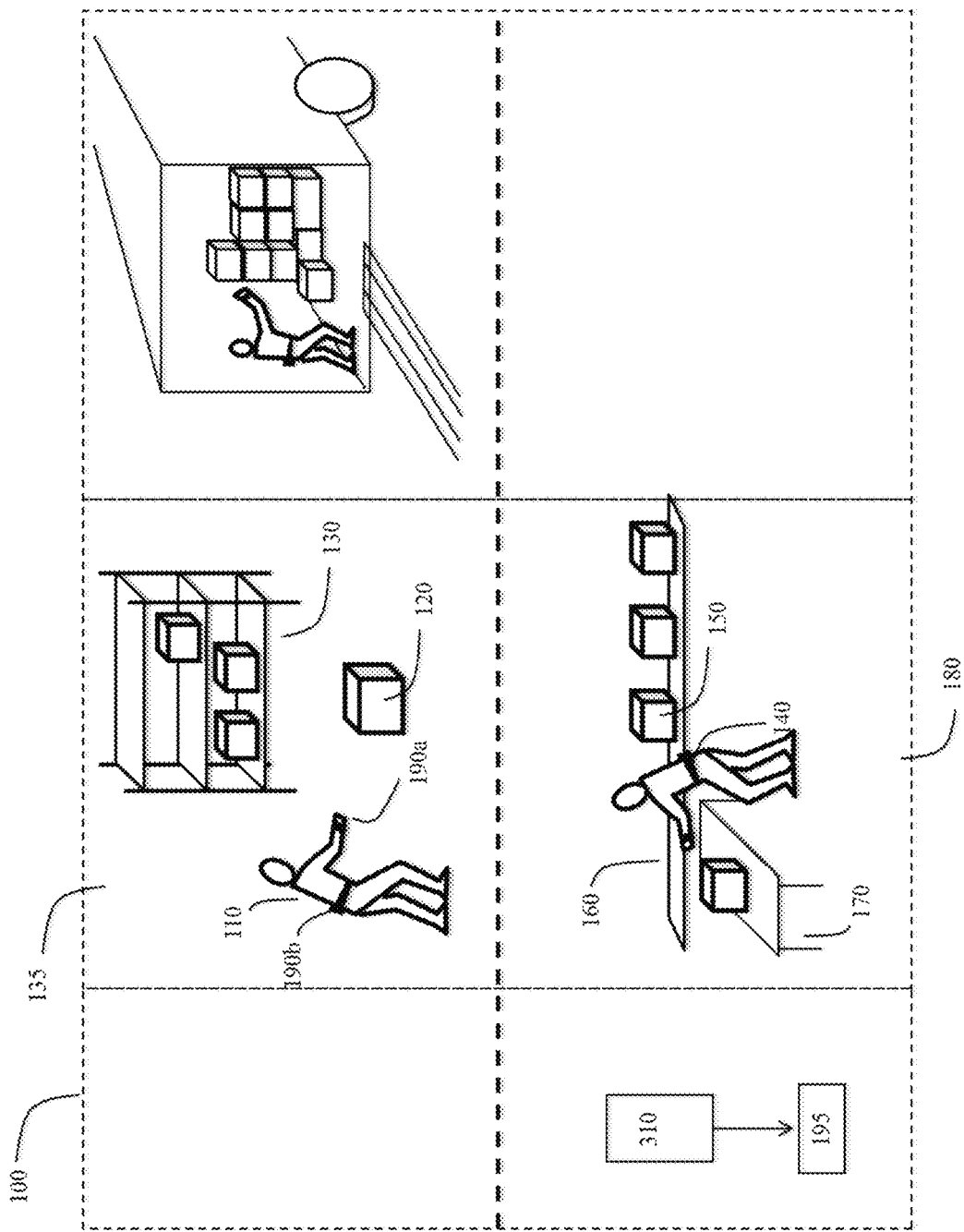
FIG. 1 illustrates a physical environment for implementing a method for monitoring safety.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

This disclosure describes the best mode or modes of practicing the invention as presently contemplated. This description is not intended to be understood in a limiting sense, but provides an example of the invention presented solely for illustrative purposes by reference to the accompanying drawings to advise one of ordinary skill in the art of the advantages and construction of the invention. In the various views of the drawings, like reference characters designate like or similar parts.

Figure 2A:
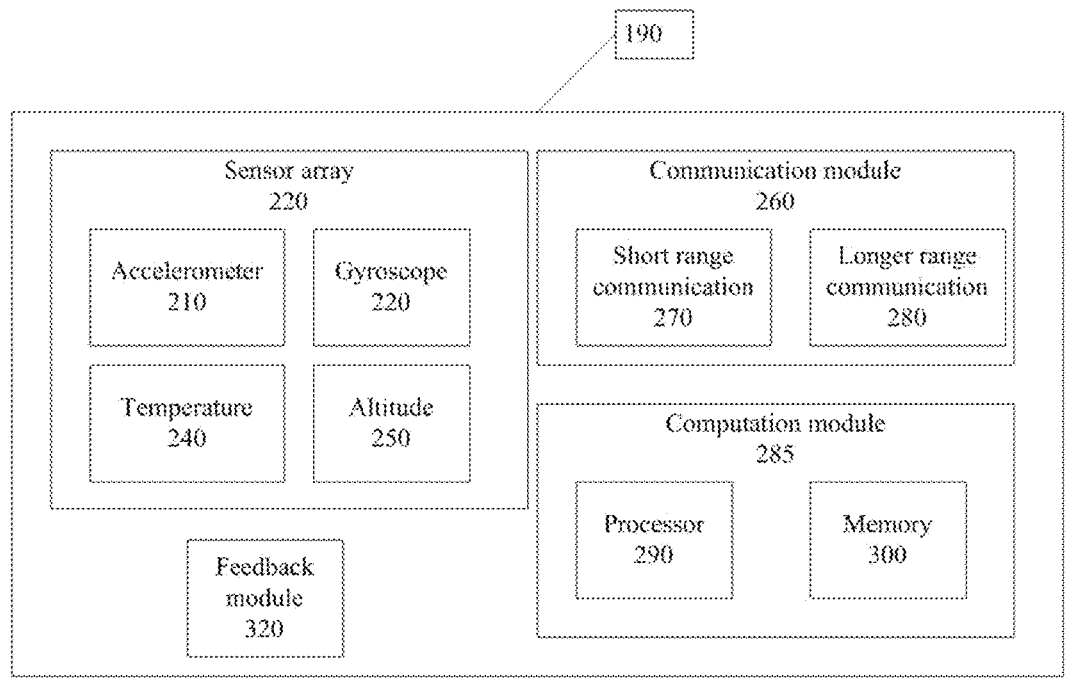
FIG. 2A is a schematic for a sensor and sensor packaging for use in implementing the method.
Figure 2B:
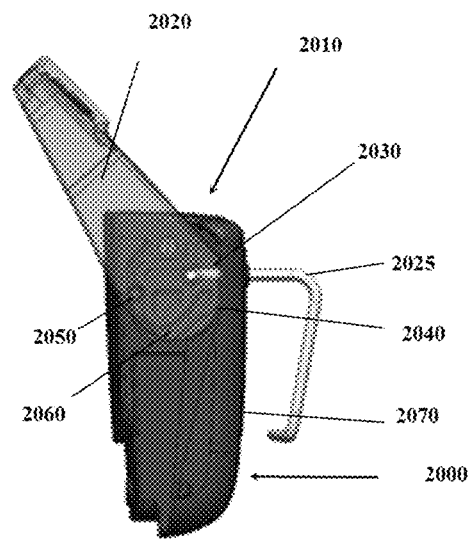
FIGS. 2B-D show a sensor packaging containing a clip for fixing the sensor to a user.
Figure 2C:
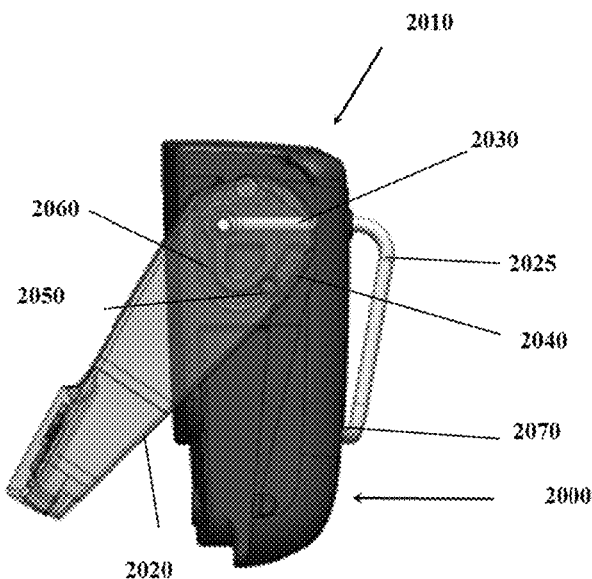
Figure 2D:
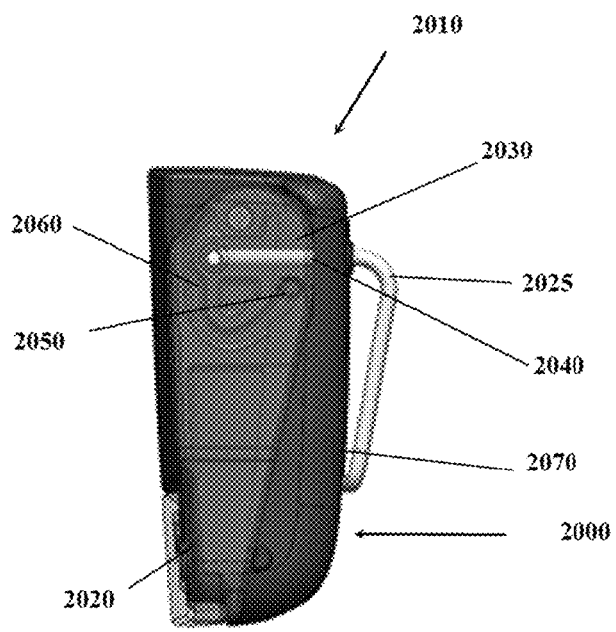
Figure 3:
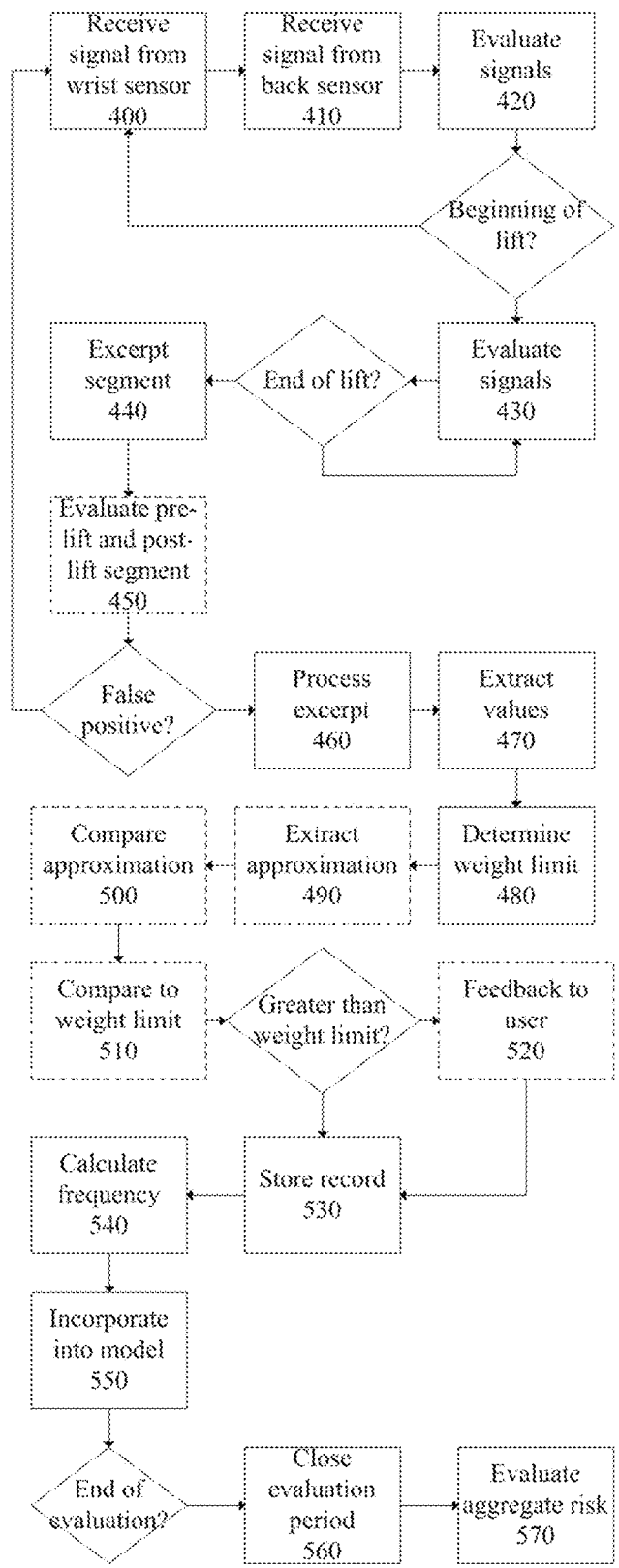
FIG. 3 is a flowchart illustrating a method for monitoring safety.

FIG. 1 illustrates a typical environment in which the system and method monitoring safety and productivity is deployed, FIG. 2A is a schematic for a sensor implementation for use in the method, FIGS. 2B-2D show one example of a sensor housing for the sensor of FIG. 2A, and FIG. 3 is a flowchart illustrating such a method.

As shown in FIG. 1, workers, or other users of the systems and methods described herein, may be deployed to various locations within a warehouse 100 and may be required to perform a variety of repetitive material handling tasks at each location. For example, a first worker 110 may lift an object 120 from the floor to a shelf 130 in a first sector 135 within a warehouse 100, while a second worker 140 may lift a separate object 150 off of a shelf 160, rotate, and transfer it to a table 170 in a second sector 180 of the warehouse 100.

Each of the first worker 110 and the second worker 140 would typically be wearing at least one sensor device, and in some embodiments, two sensor devices, 190a, b for recording movement. Typically, where two sensors are provided, the sensors used may be a wrist sensor device 190a, ideally located on the wrist or forearm of the dominant hand, and a back sensor device 190b, ideally located approximately at the height of the L1 and L2 vertebrae, but other sensor device types may be implemented as well. The wrist sensor may incorporated into a wrist device, such as a bracelet or a wristwatch, and the back device may be incorporated into a chest strap, weight belt or back brace, for example. Where only one sensor device 190 is provided, it is typically applied to a worker 110, 140 on or near the worker's hip. However, the device may be applied elsewhere and the necessary dimensions and measurements may be extrapolated from data recorded from the sensor device 190. The sensor device 190 may take a variety of forms, and is referred to herein as any of a sensor, a device, or a sensor device.

Accordingly, a single sensor device 190 may be used to record movement. Such a sensor may be mounted on a user's belt 190b and may be used to predict or estimate motion of the user's back and spine based on movements of the user's hip. A system implementing such a sensor may be trained using a machine learning predictive model trained by collecting data from sensors attached to a user's spine and comparing that data to data collected at the user's hip. After training such a predictive model, the single hip mounted sensor device 190 may be used to evaluate movement of a user's spine.

Figure 4A:
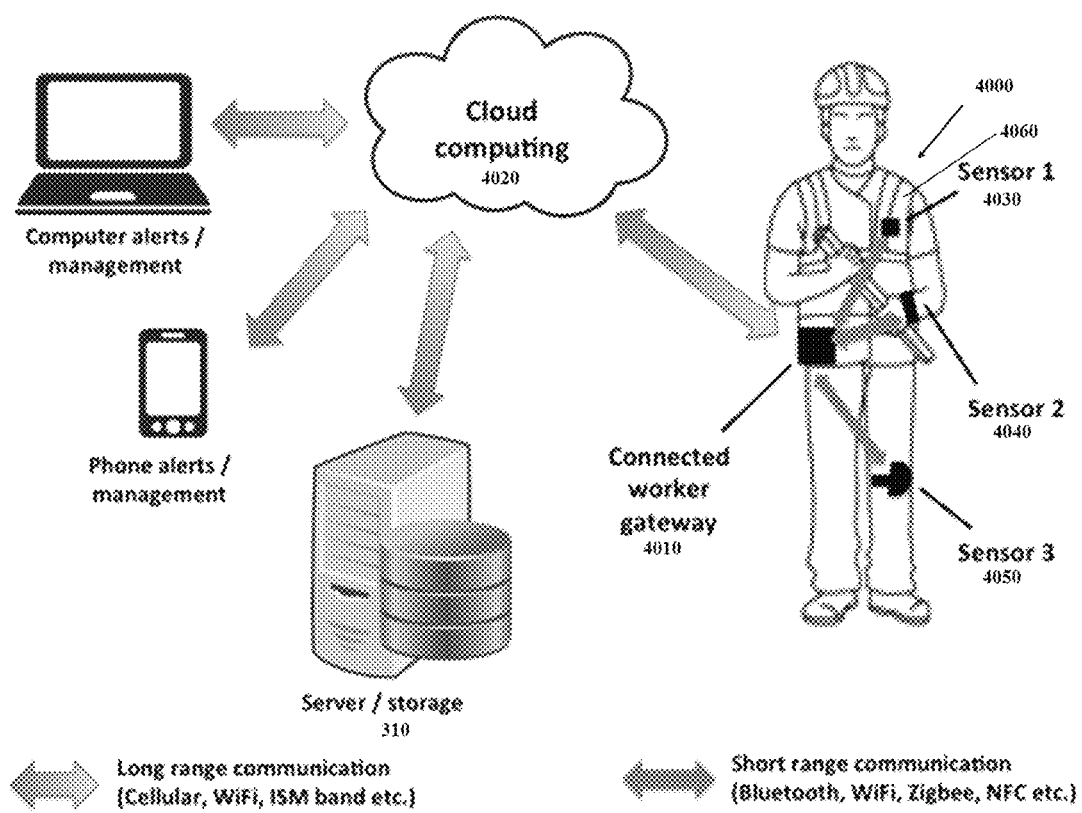
FIGS. 4A-C show systems in which the sensor and sensor packaging may be implemented.
Figure 4B:
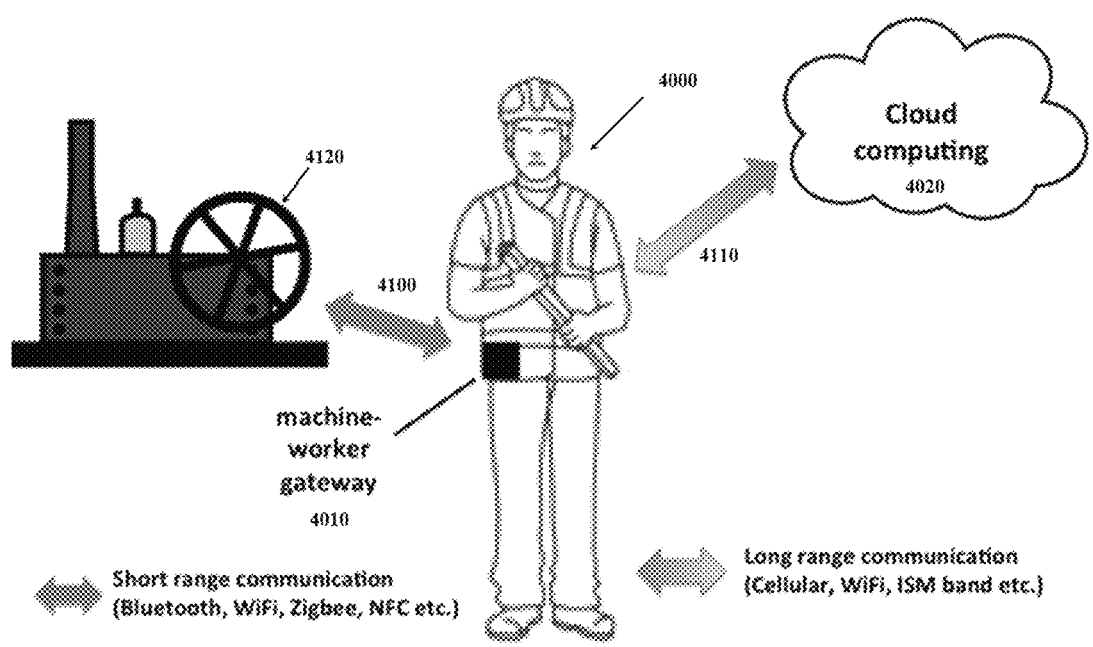

In some embodiments, a single primary sensor device 190 may be used and it may communicate with various sensors or transmitters on different parts of the user's body, as shown in FIG. 4A, in an environment in which the user is working, as shown in FIG. 4B, or on equipment the user is using. For example, a user may have a primary sensor device 190 that interacts with safety equipment worn by a user or with a humidity, temperature, or gas sensor located in a factory.

A server 310 may further be included in the warehouse 100 for receiving data from the wrist sensor 190a and the back sensor 190b and storing records of activity performed by workers 110, 140. In some embodiments, signals generated and transmitted by the sensors 190 are received and processed by the server 310. In some embodiments, results of the methods discussed below are generated and retained by the sensors 190 and are used to provide immediate feedback to workers 110, 140. In some embodiments, the results are transmitted to additional terminal devices 195 to be accessed by a third party, such as a manager, or by the workers themselves 110, 140. While the warehouse 100 shown includes a physical server, it will be understood that the server may be a cloud server or may be coupled to a cloud server to maintain a platform implementing the method described.

As shown in FIG. 2A, each of the sensor devices 190 may include a sensor array 200 including a 3-axis accelerometer 210, a 3-axis gyroscope 220, a 3-axis magnetometer 230, a temperature sensor 240, and an altitude sensor 250, such as a barometric pressure sensor. Each sensor device 190 may further include a communication module 260 which may include multiple communication interfaces. For example, each sensor device 190 may have a short range communication interface 270 for enabling communications between a first sensor device 190a and a second sensor device 190b worn by a single user. The short range communication interface 270 may further be used to receive signals from additional sensors or devices on the user's body, such as safety equipment, or from sensors or other transmitters in the user's immediate environment. The sensor device 190 may further contain a longer range communication interface 280 for connecting, for example, to a Wi-Fi or cellular network. Each sensor device 190 may further include a computation module 285, including a processor 290 and a memory 300.

Accordingly, each of the sensor devices 190a, b, may communicate with each other, or other local devices or sensors, using the short range communication interface 270 and with the server 310 or a cloud network using the longer range communication interface 280. Signals generated by the sensors devices 190 may be processed at the individual devices, may be combined with other data acquired through the short range communication interface 270, or may be transmitted to the server 310 or another centralized platform for analysis.

The sensor devices 190 may further incorporate a feedback module 320 for providing feedback to the user. For example, the feedback module 320 may include a motor for generating vibration and providing haptic feedback, or audible feedback in response to the output of the method. Further, different levels or patterns of vibration in the context of haptic feedback may be used to indicate different alerts to the user of the device. The sensor devices 190 may further incorporate user input means by which users can control the sensor device 190. For example, the device may include modules for detecting and interpreting voice or gesture based commands.

The sensor device 190 may have an additional module for determining location by, for example, incorporating a GPS unit or other geolocation components and processes. Alternatively, or in addition to geolocation components, the sensor device 190 may include a module for triangulating the location of workers based on proximity to known landmarks, such as beacons.

The sensor devices may further include batteries for providing power to the various modules therein. The sensor devices may further incorporate LEDs, displays, or other methods for delivering feedback to the workers 110, 140 wearing the sensors. For example, the device may utilize a display to display the risk metrics, or a goal, rank or other relevant information like battery and signal status. Other information can be error or warning messages when a user is detected to not be wearing the device correctly. The device can also show information like number of steps taken by a worker, calories burned, active hours in the shift, current time and the time to next break etc. This information can be shown when a worker requests it, at regular intervals, or automatically when one of the methods described below are used to identify a relevant or hazardous situation.

In some embodiments, the user interface is replaced by, or supplemented by, a separate portable device or an application for use on a smartphone. In such a case, when an alert is triggered, such alert may be transmitted to a user on his smartphone.

FIGS. 2B-D show a sensor packaging 2000 containing a clip 2010 for fixing the sensor device packaging 2000 to a user. The sensor device 190, as discussed above, must be attached to the body of a user, typically in a predetermined location or in one of several potential predetermined locations. Once attached, the relative motion between the user's body or clothing and the sensor device 190, which would be noise in a signal generated by the sensor, should be minimal. Accordingly, a robust fixation mechanism, combined with appropriate calibration methods, described below in more detail, are useful to reduce signal noise and increase the accuracy of the various methods described.

FIG. 2B shows a sensor packaging 2000 having a clip mechanism 2010 in an open position for fixing the sensor to a user's clothing. The clip 2010 includes a lever 2020 which, when rotated, converts its rotational motion into horizontal motion of a clip, such as wire clip 2025, using a cam mechanism 2030. The cam mechanism 2030 uses a cam surface 2040 and a pin 2050 interacting with a track 2060 in order to implement horizontal motion in the wire clip 2025. When the lever 2020 is fully lifted, as shown in FIG. 2B, the wire clip 2025 is separated from a back surface 2070 of the sensor packaging 2000, providing a space for the user to place the device over their belt or trouser rim. As shown in FIGS. 2C-D, once the sensor packaging 2000 is in position, the lever 2020 is rotated towards the sensor packaging 2000, which draws the wire clip 2025 towards the back surface 2070 and then compresses the user's belt or trousers by applying a normal force to the clothing, minimizing the motion between the sensor packaging 2000 and a user's clothing.

The normal force applied by the clip design can be varied by modifying the parameters of the wire clip, which acts like a spring. The length, design and material can all be modified to obtain a required normal force. In addition, a high friction material can be placed between the wire clip and back part of the enclosure to increase the friction force between the device and the clothing. For example a rubber coating can be placed on the wire clip, or a rubber overmold may be placed on the back surface 2070 of the sensor packaging 2000. The wire clip can also be modified to increase its range of motion by adding torsion springs or other similar design methods.

The clip 2010 described may further comprise a switch activated by the closure of the clip. For example, the clip 2010 may include a magnet incorporated into the lever 2020, such that a magnetic field sensor, such as a reed switch, may be used to determine when the sensor packaging 2000 has been applied to a user's person. Accordingly, when the clip 2010 is closed on a user's belt, the switch may indicate that the sensor 190 has been positioned, and the device may initiate a calibration process, as described in more detail below. Similarly, a capacitive surface incorporated into the clip 2010 may be used to confirm that the clip has been closed. Alternatively, a physical switch or button may be included to indicate that the sensor packaging 2000 has been properly positioned, and that the sensor 190 may now begin to capture data.

While the components of the two sensor devices 190*a, b* are described identically in embodiments in which two sensor devices are utilized, in some such embodiments, the sensors comprise different components. For example, the wrist sensor 190*a* may not include a longer range communication device 280 or a computation module 280 and may instead immediately transmit signal data to the back sensor 190*b*. The back sensor may then process the data and transmit results to the server 310.

Other implementations are possible as well. For example, all signals may be immediately transmitted from the sensor device 190, to the server 310 which in turn implements the methods described. For the purposes of outlining the methods performed, the methods will be described with respect to such a platform where processing is handled centrally at a server 310. However, it will be understood that the calculations and methods described may be performed at any one of the devices 190 described, or across a combination of the devices discussed. Further, while the method described in reference to FIG. 3 discusses a system using signals separately acquired from two sensor devices 190*a, b*, all required measurements may instead be acquired from a single sensor device 190. In such an embodiment, a single signal may be analyzed. Further, while the method described detects lifting activities, other physical activities may be detected as well, as discussed in more detail below.

Accordingly, while workers perform material handling tasks and other physical activities, including lifting objects 120, the server receives both a signal from the wrist sensor 190*a* indicative of the movement of that sensor over time (400) and a signal from the back sensor 190*b* indicative of the movement of that sensor over time (410). This may be received in the form of a data stream or a transient signal, or it may be received in the form of chunks of data received consecutively.

The server then evaluates (420) both signals to determine if any portion of the signal represents the initiation of a lifting activity. If a lifting activity is identified in the data, the server then further evaluates (430) both signals to identify an end point of the lifting activity. In some embodiments, this detection of an initiation of a lifting activity and an end point of the lifting activity is by way of a rules based approach directly using variables obtained from the sensor data, or based on variables detectable after only minimal signal processing. This rules based approach may include, for example, measuring the back angle with respect to the gravity plane and determining when it passes a threshold. This type of threshold may be static or variable, depending on other elements of the lift. Arm elevation angles may further be used to detect lifts above the shoulder, for example.

In some embodiments, the signals are used to identify only an initiation of a lifting activity, but not an end point of the lifting activity. In such an embodiment, a lifting activity may be assigned a specified time limit, such that the lifting activity is assumed to have concluded after a fixed amount of time has passed.

In embodiments with only minimal signal processing prior to identifying the initiation of a lift may comprise only filtering of data to reduce noise and cancel any drift. Typically, filtering is applied, such as a band pass filter, to ensure that more resource intensive processing is applied only once a lifting activity is detected within the more minimally processed data. For example, drift in height sensor data and gyroscope data may be filtered to reduce noise prior to identifying a lifting activity, and then the filtered data may be utilized to detect the initiation of a lifting task with a reduced number of false positives.

In some embodiments, the lifting activity will be single lifting motion. In others embodiments, the lifting activity may comprise the entirety of the moving of an object from a first location to a second location. For example, the lifting activity may comprise a first user 110 picking an object 120 up off the floor and placing it on a shelf 130. Similarly, the lifting activity may comprise a second user 140 picking up an object 150 off of a shelf, rotating, and placing the object on a table 170. Alternatively, the lifting activity may be a simple lifting action in preparation for a secondary action, such as walking with the package.

Once a beginning and end point of a lifting activity is identified, the portion of the signals from the wrist sensor and back sensor between the initiation and end point of the lifting activity are excerpted (440) from the signal to generate a first segment of data corresponding to lift data from the wrist sensor and a second segment of data corresponding to lift data from the back sensor.

In some embodiments, data from the point of time of the initiation of the lifting activity is taken and is processed immediately upon detecting the initiation of a lifting activity. In such a way, risk models depending only upon static posture at the time of lifting may be implemented immediately and may provide results before the completion of the lifting activity.

Optionally, the method may then evaluate (450) a portion of the signals from the time period immediately before lift and immediately following the lift. This may be used, for example, to eliminate false positives prior to incorporating such results into statistics being reported. For example, when a worker bends over to lift something outside the scope of his task, such as a worker bending down to lift a pen from the floor and place it in his pocket. In such an example, the initial back bending angle and lowering of the wrist, as measured by wrist height, would indicate a lifting event. However, since the wrist would then align with hip of the worker and the back of the worker would straighten, this would not be considered a lifting event. Accordingly, the portion of the signal immediately following the lift may then clarify that the lift detected would constitute a false positive for the purpose of statistics being gathered.

Once the portions of the signals corresponding to lifts are excerpted, the method processes (460) the excerpted portions of the signal to extract metrics required for risk models being evaluated. The processing of the excerpted portions of the signal typically incorporates methods designed to increase signal to noise ratio and otherwise improve the quality of the data. This may include methods such as low pass filtering, Kalman filters, Gaussian moving averages etc., all of which combine to reduce the noise in the signal and remove unwanted drift of signals, such as the barometric pressure signals, from the sensor data. From the signal processing, we compute several new variables such as back sagittal angle or wrist elevation angle, as discussed further below.

In some embodiments, some amount of signal processing occurs prior to step 420 so that a signature in the data corresponding to a lifting activity may be more consistently identified. Such a signature may be used to detect sequences associated with lifting tasks, such as box grabbing, carrying, and dropping. In other embodiments, the data is checked after the excerpts have been processed to confirm that a lifting activity has indeed occurred. For example, the data from the back sensor 190*b* may be monitored to determine when a worker's back has bent over a certain amount. This information may be coupled with data from the wrist sensor 190*a* to increase accuracy. While the method is described with respect to a lifting task, it will be understood that the task may be any number of physical tasks, such as a known sequence of motions for assembling a device or a specific task such as rebar assembly within the construction industry.

Where the risk model being evaluated is the NIOSH lifting equation risk model, the method extracts (470) from the data the following values:

H—a horizontal location of the object being lifted relative to the body. This may be determined, for example, by evaluating the horizontal difference in location between the wrist sensor 190*a* and the back sensor 190*b* and accounting for known offsets based on the angle of the back sensor 190*b*, and the known thickness of the trunk of the worker being evaluated, as well as the offset from the workers wrist to his hands.

V—a vertical height of the object being lifted relative to the floor. This may be determined, for example, using a height sensor in the wrist sensor 190*a*, such as the barometric pressure sensor 250 and further utilizing some of the signal processing techniques discussed below.

D—distance the object is moved vertically. This may be determined by calculating the difference in height at the time of initiation of the lift and the conclusion of the lift. In cases where the lifting process being evaluated includes both picking up and putting down the object, this may be the difference between the highest and lowest heights measured during the process.

A—asymmetry angle is a measure of how much the workers back is twisted during the process. Where a worker 140 picks up a package 150 in a first location 160 and places it down in a second location 170, the amount of rotation of the workers back is measured and evaluated. This may be evaluated by extracting the data from the gyroscopic sensors in the back sensor 190*b* and applying an offset based on the workers trunk thickness.

F—frequency of lifts performed, as computed from lift detection algorithms.

In some embodiments, duration of lifting tasks may be implemented, as computed by the time lifting activities have occurred and have been detected by lifting algorithms.

In some embodiments, an additional variable, C, may be incorporated and evaluated to assess the quality of the grip of a worker on a package.

The processing associated with these variables, as well as those below may include computing a gravity vector from quaternion data, which is obtained from the fusion of gyroscope and accelerometer sensor data. In such embodiments, acceleration in both horizontal plane and vertical direction may then be computed using the gravity vector. Threshold based outliers may then be removed from the data. Components of the back and wrist elevation angles are then computed using components of the gravity vectors.

Several required variables may be detected or confirmed by way of machine learning algorithms. Similarly, the accuracy of lift detection may be improved by way of machine learning algorithms. Such algorithms may further be utilized to confirm the identification of the activity detected, both in terms of improving the detection of true positives and eliminating false positives. More broadly, such algorithms may improve the precision and recall of lift detection and variable evaluation. Statistical features monitored by such machine learning algorithms may include:

Lagged cross-correlations between variables;
Dominant frequency components of the signal;
Movement intensity statistics;
Movement energy statistics;
Signal magnitude area; and
Window duration.

All of these statistics may be monitored over windows of data which may be calculated based on elements of the signal, such as those detected above in steps 420 and 430.

As discussed above, some variables may be detected directly from the sensor data while others require further processing. Since several variables are inferred, rather than detected directly, the method may utilize confidence intervals in the estimates and may report results, as discussed below, in the form of either conservative or aggressive approaches, to calculate risk metrics. Such approaches may be selected by a user operating a platform implementing the methods.

The height of sensors is typically extracted from a barometer, or other types of altimeters. Data from these sensors tend to drift. Accordingly, the drift may be corrected by coupling the sensor data with acceleration data in the gravity direction in a Kalman filter. This may also be done by way of a low pass filter for certain types of altimeters. Further, the height detector may be calibrated by setting the height to a known value upon the initiation of a lift. For example, the height of a back sensor may be set to a fixed value at the beginning of each lift, regardless of whether the worker is, for example, standing on a stool.

In some embodiments, some initial signal processing is applied to the signals upon receipt so that the detection of the beginning of a lifting activity may be made with more accuracy. The initial signal processing may then be followed by more advanced signal processing and machine learning algorithms for extracting remaining variables from the data and for confirming that a lift actually occurred during the time period excerpted from the signal.

Besides travel distance for a specified value between the beginning and conclusion of a lifting activity, each variable may be independently evaluated with respect to the beginning of a lifting activity detected and at a conclusion of a lifting activity detected. For example, where a worker 140 moves a package 150 from a shelf 160 to a table 170, if the worker faces the shelf while doing so and twists his back 90 degrees to deposit the package 150 on the table 170, his angle will be 0 for the beginning of the lifting activity and 90 for the end of the lifting activity.

Other ergonomic risk models may be implemented as well, and may require extracting different values from the data. For example, if implementing the risk model developed by Marras et al using his Lumbar Motion Monitor, the data extracted from the signals may be:

Average twisting velocity of the torso during the lift activity, computed in a way similar to the calculation of the asymmetry angle discussed above, except using angular velocity.

Maximum moment on the lower back, which is computed by multiplying the maximum horizontal distance between the load and the worker's trunk and the weight of the object lifted.

Maximum sagittal flexion of the torso, which is determined by extracting the offset bending angle of the lower back relative to a vertical axis (usually gravity).

Maximum lateral velocity of the torso, which may be determined from the accelerometer gyroscope in the back sensor.

Frequency of lifts specified in lifts per minute, which can be obtained from the frequency of lift detection.

In some embodiments, the risk models specified may be used to calculate a maximum recommended lifting weight based on a workers lifting technique. This is done by using the variables extracted from the signals in a risk model. For example, the NIOSH risk model may be used to calculate a recommended weight limit. Further, the model may be used to calculate a lifting index identifying a risk associated with any particular lifting action or task. Either model may provide numerical results, or those results may be classified in terms of low, medium, and high risk lifts. Similarly, underlying values for variables may be implemented directly in the models, or they may be mapped on to low medium or high values.

Using the NIOSH risk model as an example, a recommended weight limit for a single lift may be calculated by simply determining each of the values discussed above, determining an appropriate multiplier used in the model (typically determined from a table associated with the model, or by calculating an appropriate ratio) and multiplying the relevant multipliers. Accordingly, the recommended weight limit may be determined from the equation RWL=LC*HM*VM*DM*AM*FM where LC is a constant multiplier for the formula, typically 51 lbs., and HM, VM, DM, AM, and FM are the multipliers associated with the calculated values of H, V, D, A, and F respectively. In some embodiments, an additional multiplier may be used to incorporate the duration of lifting tasks. While the NIOSH risk model is described, other risk models may be implemented as well. Further, by dividing an actual weight lifted by the recommended weight limit generated by the NIOSH model, a lifting index may be generated providing an evaluation of the risk associated with a specified lifting activity.

Further, data from individual workers may be correlated with personal information for that worker. For example, a specific worker's data may be correlated with that workers height, history of back injuries or other medical issues, or other physical or personal characteristics that may affect performance. Further, measures of physical characteristics may be estimated, such as arm length for workers, which can in turn be used to improve both the ability to infer variable values from signal data and the ability to use the variable values detected.

While NIOSH and Marras models are described, other risk models may be utilized as well, such as Liberty Mutual® tables, RUBA, RULA, and others. For example, the signals from the sensor 190 may be used to estimate the compression at a specified vertebrae of the spine using a biomechanical model. That compression may then be compared to a maximum limit, such as the 770 lbs. prescribed by OSHA, in order to classify a lift as potentially high risk.

In this way, the selected risk model is used (480) to determine a maximum recommended weight for any given lift. Where the risk model used supports a determination for a single point in time, the risk model may be implemented immediately following the detection of an initiation of a lifting activity at step 420. In such an embodiment, the information from the moment of time detected is immediately extracted and processed.

Optionally, the method may extract (490) from the data an approximation of the actual weight of a package lifted. Such an approximation may be calculated by evaluating the angular velocity or acceleration of the wrist sensor 190*a*. In some embodiments, this may be compared (500) to the same metric for a known weight such that the weight of an object may be inferred by comparing the angular velocity of a specified lift by a worker to an angular velocity associated with a lift for a known weight by the same worker. The accuracy of this measurement may be further improved by evaluating data related to the angle of the back sensor 190*b* and similarly mapping it to known angles for known weights by the same worker.

Similarly, metrics correlated with energy applied during a lift may be implemented. Such metrics may draw signals from both the back and wrist sensors and may be used to evaluate the weight of an object lifted.

The various signals evaluated upon identifying a lifting motion may then be used to detect acceleration in the vertical direction in the world frame of reference. Accordingly, when a worker begins a lifting process, the wrist based accelerometer may immediately detect a jerking motion as the height sensor begins to rise from its lowest position. The velocity of the rising motion may then be used as a proxy for effort applied in lifting, which in turn may be used as a proxy for determining the weight of an object lifted. Such an approach may determine both the weight of the object being lifted or, if the weight of the object is known, the fatigue of the worker lifting the object. Either approach will allow the system to determine an effective weight of the object from the perspective of the worker. Including the fatigue of the worker lifting the object in this way may further incorporate a fatigue component in evaluating risk to the worker.

In such an embodiment, the approximate weight or effective weight calculated is then compared (510) to the maximum recommended weight (determined at 480) based on the model.

If the weight lifted is greater than the maximum recommended weight, the sensor may provide feedback (520) to alert the worker to the weight limit. Such feedback may be, for example, haptic or audible feedback. In some embodiments, a combination of feedback methods may be implemented, and the feedback may then be displayed on a screen associated with the device or through an LED, and haptic feedback may be implemented to prompt the user to view the screen.

While the method evaluates individual lifting activities, the server will continue to receive data from the sensor devices 190*a*, *b*. Accordingly, the server may then store (530) a record of the first lift in a memory associated with the server and return to step 400 and continue monitoring the sensor data to determine if the worker is performing additional lifting activities. The server typically continues to monitor the data for additional lifting motions over the course of an evaluation period. In some embodiments, once multiple lifts have occurred, the method calculates (540) a frequency associated with the lifting motions identified and incorporates (550) that value into the risk models in order to monitor and evaluate risks associated with repetitive lifts. Such frequency data may be used in the NIOSH model described above, for example, to reduce the maximum recommended weight for a repeated lifting activity based on repetitive stresses and associated risks.

After the conclusion (560) of an evaluation period during which lifting motions are evaluated, the risk models may be used to evaluate (570) aggregate risk over the time period. In some embodiments a worker's shift may be divided into blocks of time, such as half hour blocks, for use as evaluation periods. In some embodiments, the evaluation period is instead the entirety of the worker's shift.

In addition to lifts detectable by the platform described, a variety of other events are potentially detectable. These other events may include actual risk indications, as well as behaviors indicative of potential risk. For example, jerky, or sudden motion put extra strain on a worker's body, and such jerks may be identified by identifying spikes in the acceleration data. The amplitude of the spikes along with their distribution over time can be used to determine the intensity of and frequency of a jerk. If such jerks are overly frequent, or overly aggressive, a safety manager may be alerted to the activity.

Similarly, jumps can be detected and impact on the health of knees can be inferred. For example, a distribution worker might jump off of a truck with or without package in hands. The impact of jump on the knees can be detected by looking at spikes in the acceleration in the vertical direction and correlated with sudden changes in detected height. The magnitude of the acceleration and height when the jump occurs can give an indication of the intensity of the impact. This can be reported, and feedback provided to reduce the number of jumps that occur, or in order to reduce the intensity of the jumps. These jumps can often lead to impact and cumulative injuries on knees, ankles and hips.

In one embodiment the device could measure running within a facility where running is not recommended, or where surfaces could be conducive to slipping.

In another embodiment, the device could be used to measure when someone is climbing up a ladder, and the amount of time spent on each part of the ladder, or if a user is using an elevator, by monitoring a change in the user's elevation. The rate of change of height can help determine the action being performed.

In another embodiment, slips which do not lead to falls can also be detected, and considered as near misses. In addition, these episodes can also be used to log information about incidents, such as the time, and to which worker they happened to.

In another embodiment, the device can be used to evaluate the driving of vehicles such as trucks and forklifts, or the use of other industrial equipment. Based on the acceleration and deceleration profiles, driving can be evaluated and scored. The number of hard braking actions or extreme acceleration can be tracked. Speed of the vehicle can be estimated and if it surpasses a certain threshold, then action can be taken. In addition, if the vehicle is involved in an accident or an impact, it can also be detected and timestamped and data of the impact can be preserved for future investigation.

Further, an activity log for a user over time can help determine if they are exposed to gradual risks. The platform described may detect a number and frequency of repetitions doing a specific task, a number of steps taken, and an amount of motion, vigor of motion, time spent seated or standing or moving. These various factors can help determine the amount of fatigue and necessary resting period to help recover. As discussed below, the system may further incorporate environmental factors, such as localized humidity, in order to refine a model for the amount of fatigue a user might be experiencing. The activity log may also be used to evaluate user productivity, as discussed in more detail below.

Further, the platform monitors the user's orientation at any given time. In the event of a falls or stumble, the device can determine the severity of the fall by measuring the acceleration and angular velocity. Using the orientation, the invented device can also determine if the worker has been in an improper orientation for an extended period of time, and can trigger an alert or an alarm to prompt appropriate action. Further, the platform could measure falls happening on the same level or falls happening on different levels. The combination of acceleration, direction of gravity on the device, and the change in height would allow the detection of a fall, and also the position of the worker on the ground.

In addition to the identification of particular activities based on extraction of orientation and acceleration data from the sensor device 190, additional context may be provided for the data by sensors or communication protocols used to calculate a user's location within a facility or a distance from another object. For example, in an indoor facility, beacons may be distributed, and Wifi or Bluetooth signal strength or triangulation may be used to estimate the position of the invented device inside the facility. Similarly, in an outdoor environment, GPS can be used to estimate location. In some embodiments, distance from a known object may be estimated based on signal strength between the sensor device 190, and a device or beacon at a known location relative to the object.

Information about the worker's location may allow for identifying additional user activity as well as user physical activity with increased accuracy. For example, if the platform detects that a user has entered a region for which he is not authorized, the device may trigger an alert to the user or the user's supervisor.

Further, by locating multiple users and pieces of equipment, the platform may detect when a user comes within a threshold distance of a moving piece of equipment, such as a heavy truck or forklift, and may trigger an alert to the user.

Further, the device 190 may determine if a worker has collided with a moving vehicle or is otherwise injured by detecting any impact through the accelerometer, evaluating a resting orientation of the user, and/or using location information to determine the distance to an object in order to determine the cause of an impact. In those cases, the device may vibrate to alert the user and/or send an SOS to the server 310 and potentially alert emergency responders.

In some embodiments, the sensor device 190 may also be used to time stamp when a user comes into work, takes a break, or ends work by confirming the time period for which the user is within a work zone. Further, while a user is at work, location can be used to assist in determining an activity performed, as a user location can be correlated with detected motion in order to label physical activity based on time or location. Further, in determining the particular activity performed, the user location can be used to determine what activities would be expected to be performed in a particular location.

The sensor device 190, together with the activity detection methods described, may provide additional insight into the productivity of workers and/or facility design.

Activity logs for individual users may be reviewed to evaluate, for example, the number of times a user performs a specified activity, and how long the activity takes, among other data points. This information may then be mapped and optimized. For example, mapping and breaking down the tasks performed by a warehouse associate who is fulfilling an order will show them picking up an order in a first location in warehouse, walking to a specific shelf location to check inventory, spending three minutes searching for the specific item, walking to a boxing and shipping location, and leaving the box on a pallet for pick-up by a package delivery company. This information may be recorded for several employees, and the warehouse or process could be redesigned in order to optimize the most common activities. This may be by relocating goods or by reassigning tasks based on differences between users of the system.

In the context of project management and validation, the systems and methods described may be used to confirm that users have performed required tasks. For example, on a construction site the sensor device 190 could be used to determine what time an electrician clocked in, which floor they spent most time on, an amount of motion and activity measured, how long they spent working in that location, and how that compares to what was planned for the day. Invoices can be generated based on this data, as well as progress reports for specific projects. Further, worker efficiency may be evaluated based on the correlation between an actual log of physical activity generated by the methods described herein using the wearable device 4010 and a user schedule identifying expected activities for the user.

Productivity metrics may be developed and utilized based on frequency of detection of certain activities. Such data may be analyzed to search for relationships with other detected metrics. For example, productivity can be correlated to changes in dehydration as measured by sweat sensors, such as in the system discussed below in reference to FIG. 4B, or to times of the day, weather, or ambient or body temperature.

FIG. 4A shows a system in which the sensor device 190, described generally as a wearable device 4010, may be implemented. As shown, a user 4000 may be provided with a wearable device 4010. The wearable device 4010 typically includes multiple communication interfaces, as discussed above. This allows the device to connect to servers 310 either directly or through a cloud computing interface 4020, in order to upload and receive information, as well as additional sensors 4030, 4040, 4050 on the user's body which may communicate with the wearable device 4010 and may be provided to keep the user productive and safe. These additional sensors 4030, 4040, 4050 may be applied directly to the user's body, as in the case of sensor 4040, or may be integrated into safety equipment, such as sensor 4030, integrated into a harness, and 4050, integrated into a kneepad.

The multiple communication interfaces may provide an ability to communicate data in real time, including warnings and alerts, through the wearable device 4010, using long range communication methods like 900 MHz and cellular radio as well as short range communication methods, such as WiFi and Bluetooth. In some embodiments the wearable device 4010 may further provide a local wired port, such that sensors may be connected using, for example, a USB connection.

The sensors are typically small and use low power communication like Bluetooth Low Energy to send warning messages, and may be, for example, a gas detection sensor. Warning messages may be received at the wearable device 4010 and communicated in real time to the wearable device 4010 in order to trigger an alert, where appropriate. Alternatively, the wearable device 4010 may receive raw data from the gas detection sensor which may then be evaluated at the wearable device 4010, and may trigger an alert when an unacceptable level is detected.

The sensors may be integrated into safety equipment, such as the harness 4060 containing sensor or transmitter 4030. In such an embodiment, the wearable device 4010 may determine if a user is performing a task or is in a location in which such a harness 4060 is required. If so, the wearable device 4010 may require confirmation that the harness 4060 is present and is securely attached before authorizing a user 4000 to perform an activity. For example, in order to determine if such a harness 4060 is required, the wearable device 4010 may detect the altitude of the user, and if the user is at a high altitude and proper usage of the harness 4060 is not detected, the wearable device 4010 may alert the worker and ground personnel.

In some embodiments, the wearable device 4010 has onboard memory and processing capability, such that the device may save and analyze data to determine if real time feedback to the worker or to an external entity is necessary and, if so, communicate this feedback. Alternatively, or in addition to such on board processing, some portion of the data analytics may be done on cloud servers or local servers upon receipt of the data from the device, as opposed to in real time.

Another potential communication method involves pairing the wearable device 4010 with a gateway residing within the communication range of the device. For example, using long range 400-1000 MHz signals to send the data from the device on a worker to the gateway within one mile radius. The gateway can rely on satellite communication at remote locations to send the data in real time to the external entity. In some implementations, such as on construction sites, a trailer with a communication hub may be provided, and the communication hub may then connect to the individual users of a system implementing the methods described.

In some embodiments, the additional sensors, such as the wrist sensor 4040 may use the wearable device 4010 as a gateway for relaying information to a server, or as a centralized processing unit. Accordingly, the wrist sensor 4040 may detect information about the user, such as pulse rate, temperature, and hydration. This information may be detected directly, or it may be derived, such as deriving dehydration by evaluating skin conductance or sweat detection. The wrist sensor 4040 may then send the data to the wearable device 4010 for analysis, and the wearable device may then provide recommendations, such as a recommendation to rest or drink water. Further, as discussed above, the data recorded may be correlated with other data collected in order to, for example, evaluate the effect of dehydration on productivity.

Further, the invention can be employed to ensure compliance with Personal Protective Equipment (PPE) policies, such as confirming that a user is wearing gloves, hard hats, eye glasses, as well as other safety equipment, such as harnesses, in appropriate situations.

As an example of PPE compliance, eye protection glasses can have a low power Bluetooth transmitter monitored by the wearable device 4010. If a user forgets their eyewear and walks out of range of the transmitter contained therein, the wearable device 4010 can notify the worker.

Similarly, the wearable device 4010 may monitor activities to determine if an activity being performed is authorized for a particular user 4000 or requires particular safety equipment. As an example, a forklift may have an NFC, RFID, or Bluetooth transmitter. When a worker approaches the forklift, the wearable device 4010 may determine if the user 4000 is authorized to drive that forklift, and may confirm the proper use of safety equipment, such as a harness. If a user 4000 is not authorized to perform an activity, the wearable device 4010 may trigger an alert to a manager.

In some embodiments, the wearable device 4010 may function as a key for equipment, such as the forklift, and may transmit an activation signal for the equipment where appropriate. Accordingly, the wearable device 4010 may transmit such a signal only if the user is authorized to use the equipment, and if the user is using all required safety equipment.

FIG. 4B shows an additional system in which the sensor 190 may be implemented. As shown, the user 4000 may similarly be provided with a wearable device 4010 which includes multiple communication interfaces. As shown, short range communication interfaces 4100, such as Bluetooth, WiFi, Zigbee, or NFC may be provided to communicate with local devices, machines, or sensors, while long range communication 4110, such as cellular service, ISM band, or a longer range WiFi platform, may be provided in order to allow for communication with a cloud computing platform 4120 or a server 310.

In such a system, the short range communication 4100 allows the wearable device 4010 to communicate with the local environment. For example, a machine 4120 on which the user is working may be equipped with sensors to assist in diagnostics. Accordingly, the status of such machines may be provided to the user when the user approaches that particular machine.

Similarly, the machine 4120 may communicate with the wearable device in order to assist the various methods described above to identify a particular physical activity in which the user is engaged, or in order to allow the wearable device 4010 to determine if any safety equipment should be required for the user.

As another example, in such a system, multiple environmental sensors may be distributed throughout a work environment in order to monitor various environmental data, such as local humidity or temperature, or to detect danger, such as elevated gas levels. Accordingly, the wearable device 4010 may retrieve data from a local environmental sensor when the user is within range of the individual environmental sensors.

Such environmental sensors may be provided with transmitters with minimal communication range in order, for example, to preserve battery life or prevent interference. However, in some embodiments, the information from those environmental sensors may require centralized processing. Accordingly, when the wearable device is within range of such an environmental sensor and retrieves data from it using the short range communication interface 4100, it may then relay that data to the server 310 using the long range communication interface 4110.

Accordingly, in such a system, the server 310 may be configured to record the environmental data in a database with the identification of the corresponding sensor from which the data was acquired. By maintaining the data from multiple environmental sensors acquired at various times by multiple users, the system may achieve high resolution data by receiving, for example, humidity data from humidity sensors distributed across a work environment when any of several users 4000 of the system described walks past such a sensor. This data may then be analyzed and monitored for changes. If, for example, a gas level or pressure level spikes, or data otherwise differs drastically from an expected data point, an alert may distributed to all users. Similarly, information from sensors in different locations may be monitored, and if adjacent environmental sensors show different environmental data, the sensors may be checked for either localized problems or sensor errors.

Figure 4C:
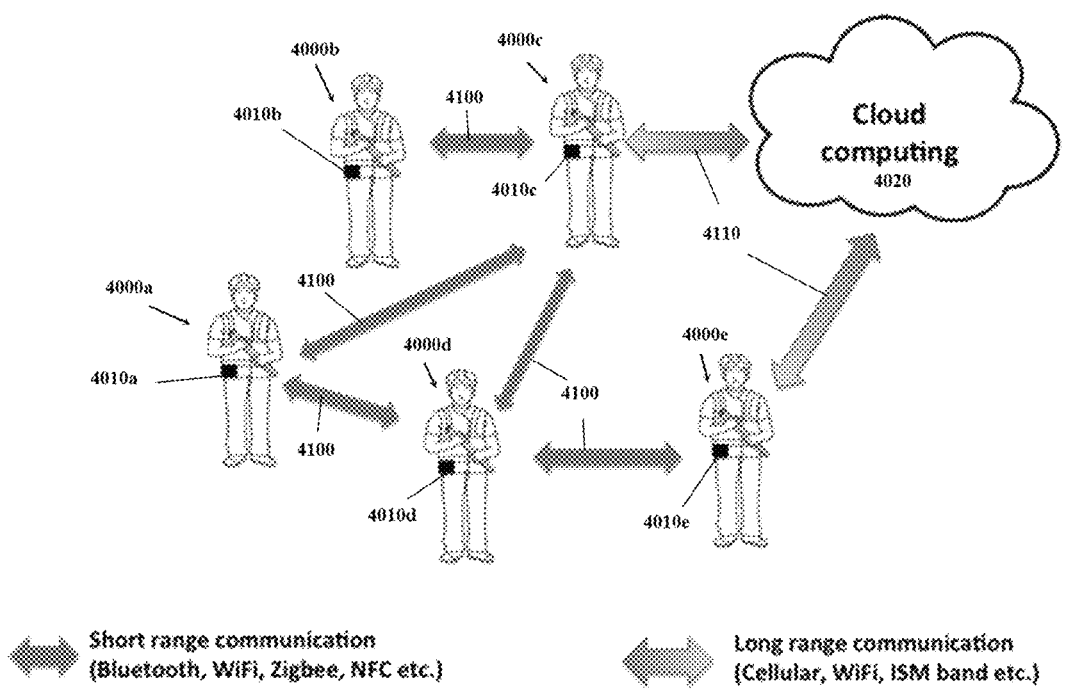

FIG. 4C shows an additional system in which the sensor 190 may be implemented. As shown, the user 4000 may similarly be provided with a wearable device 4010 which includes multiple communication interfaces, as in the system shown in FIG. 4B. However, in such an implementation, the short range communication interface 4100 provided may be used by a first user 4000a to communicate with additional users 4000b-e in order to bypass long range communication, or to pass a signal to different users 4000c within range of long range communication 4110 when the first users 4000a is out of such range.

Such a system may be implemented in order to increase the overall range of the system, such that when wearable device 4010a of a first user 4000a is out of range of the cloud computing platform and therefore cannot relay information to a server 310, it may instead relay information to a wearable device 4010c of a secondary user 4000c which can in turn relay the data to the cloud computing platform 4020. Accordingly, while the system described in reference to FIG. 4B discusses the relaying of data using the long range communication interface 4110 to transmit the data to a server 310, the system could instead relay to other users 4000b.

The system may further be implemented in order to use mesh networking protocols, such as Zigbee, to have wearable devices 4010a-e communicate directly with each other. For example, the wearable device 4010a of the first user 4000a may detect some risk, such as elevated gas levels. The wearable device 4010a may then trigger a warning in nearby wearable devices 4010b-e.

A system in which user wearable devices 4010a-e may communicate directly with each other may also support direct messaging between users.

Figure 5:
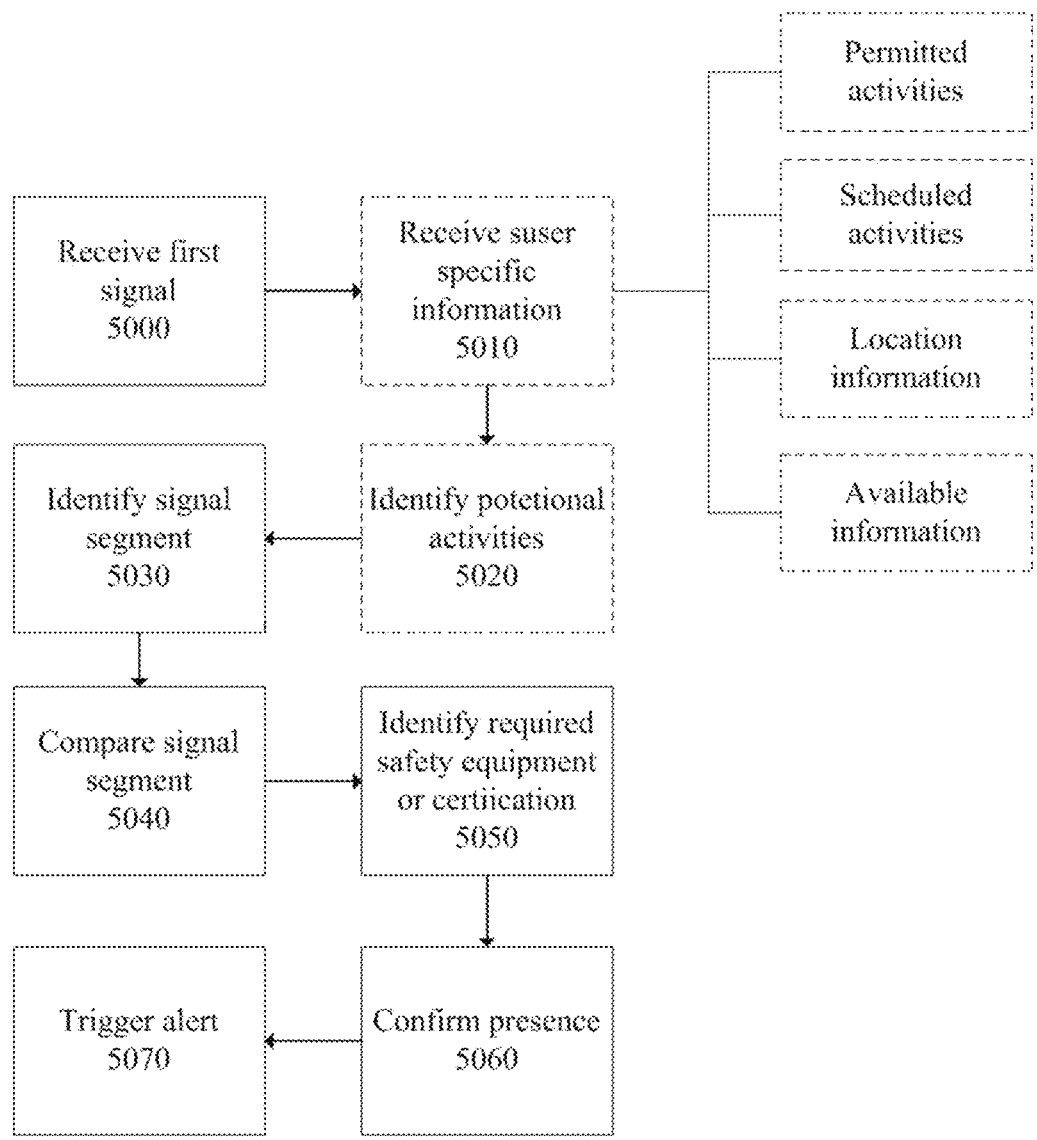
FIG. 5 illustrates a method for enforcing safety rules.

FIG. 5 illustrates a method for enforcing safety rules implemented in the systems shown in FIGS. 4A-C. As shown, the method first receives (5000) a first signal from a user's wearable device 4010 indicative of physical characteristics of that wearable device over time. In some embodiments, the method may be further provided (5010) with additional information specific to the user, such as permitted or scheduled activities for that user, or information related to a location. In such embodiments, the method may then identify (5020) based on the additional information a set of physical activities that could be expected to occur either by the particular user or at the user's location. For example, if the user is at a high altitude, or at a loading dock, specific physical activities may be expected. Similarly, the method may receive information related to objects or industrial equipment present at the location. For example, if a user is determined to be adjacent a forklift, that user could be expected to drive the forklift.

The method then identifies (5030) in the signal a signal segment corresponding to one of several expected physical activities and compares (5040) that identified signal segment to expected signal segments for each of the expected physical activities. Once a particular physical activity is identified, the method may identify (5050) specific safety equipment or certifications as required for the physical activity and may confirm (5060) that the item of safety equipment or certification is present. This may be implemented, for example, in the system shown in FIG. 4A by providing the safety equipment with a transmitter so that it can communicate with the wearable device 4010. In such an embodiment, the wearable device may confirm the presence of a signal from the safety equipment.

If the presence of the safety equipment cannot be confirmed, the method may trigger an alert (5070) either to the user or to a supervisor warning that the activity should not proceed until the safety equipment is used. For example, if a user is at altitude, but cannot be confirmed to be wearing a harness, an alert may be triggered by the method. In some embodiments, the method may prevent further activity by the user. For example, if the user is operating equipment without proper safety equipment, such as a user using or preparing to use a forklift without proper harnessing, the wearable device may transmit a signal to the forklift to turn off, or may prevent the forklift from turning on.

A signal from the safety equipment may, in addition to indicating the presence of the safety equipment, indicate proper implementation of the equipment. For example, a user may be notified if a harness is improperly attached, or if a hard hat is present but not being worn.

In the system shown in FIG. 4B, for example, the wearable device 4010 may be in communication with a piece of industrial equipment that requires activation. In such an embodiment, the wearable device 4010 may contain an activation key to be transmitted to the industrial equipment. In such a system, the activation key may be transmitted only if an item of safety equipment required for the operation of the industrial equipment is confirmed to be present. In such an embodiment, the activation key may be transmitted to the industrial equipment upon receipt of a confirmation signal from the safety equipment.

Further, the method may limit the types of activity it searches for based on proximity to industrial equipment. For example, when a user 4000 uses a forklift, the method may monitor acceleration and deceleration profiles to determine risk associated with the user's driving. Hard braking or extreme acceleration may be tracked, and the speed of the vehicle may be estimated. Further, any impact can be evaluated.

Figure 6:
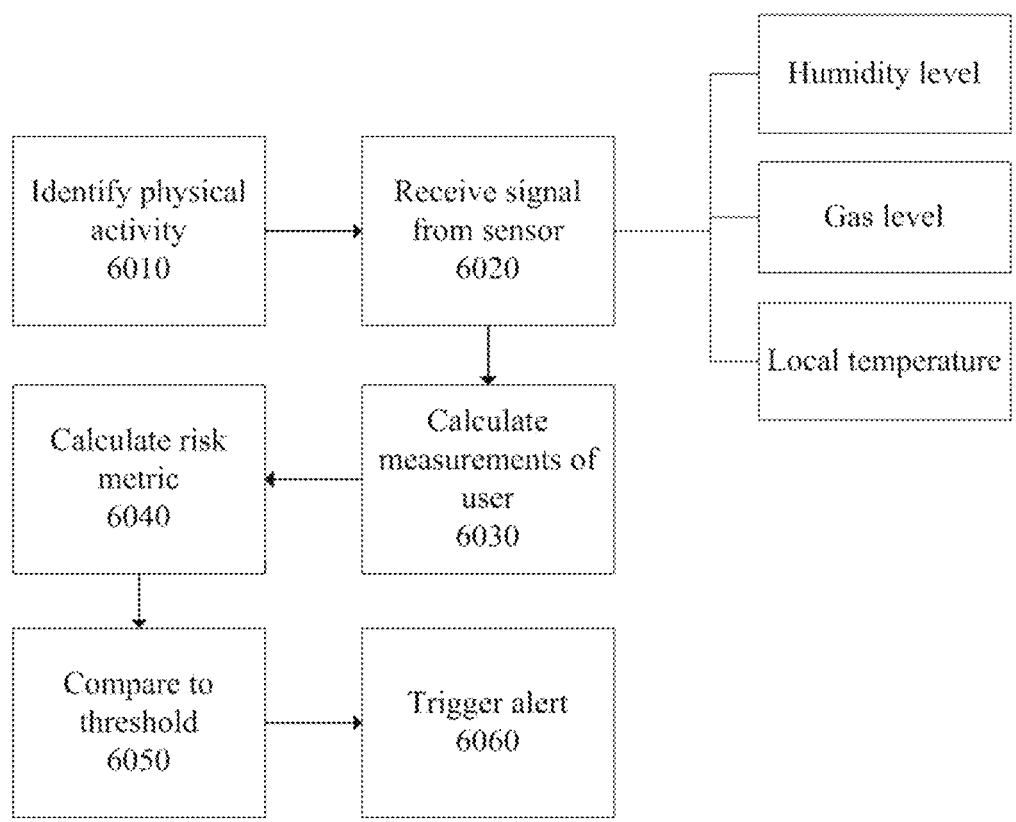
FIG. 6 illustrates a method for triggering a risk alert.

FIG. 6 illustrates a method for triggering a risk alert in the context of the system of FIG. 4B. As shown, a user 4000 may be provided with a wearable device 4010. Using, for example, portions of the method of FIG. 5, the system may first identify a physical activity (6010) performed by a user 4000 of the system based on a first signal retrieved from the wearable device 4010. The method may separately receive (6020) a signal from an environmental sensor independent of the wearable device 4010. Such a signal may provide environmental data, such as a humidity level, gas level, or temperature level for the user's location. The method may then calculate measurements (6030) of the user 4000 from the first signal for a time period corresponding to a physical activity being evaluated and may then calculate a risk metric (6040) from a risk model incorporating the environmental data received from the environmental sensor, compare (6050) the risk metric calculated to a threshold and trigger (6060) an alert of the risk metric indicates a risk level above a safety threshold.

Incorporating the environmental data into the risk metric may increase the calculated risk in certain scenarios. For example, high humidity may increase user fatigue, resulting in an increase of risk level associated with a particular activity.

Figure 7:
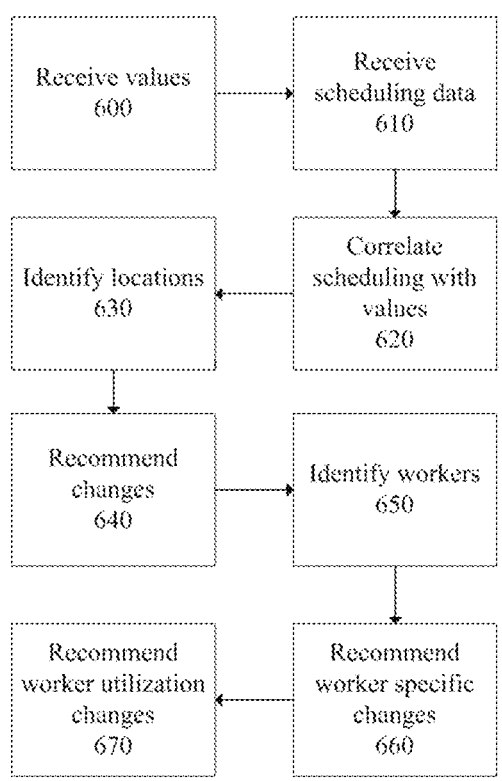
FIG. 7 illustrates a method for generating recommendations.

FIG. 7 illustrates a method for generating recommendations based on the data and risk model outputs received in the method of FIG. 3. The server first receives (600) values for the risk metric calculated in such a method with respect to individual lifting activities for multiple workers.

The server further receives (610) scheduling data for individual workers including information related to the location within a warehouse that each worker is assigned to. This scheduling data typically contains, for each worker, a location at which they would be working at any given time. The server then correlates (620) the scheduling data with the risk metric for individual lifts in order to determine a location for the individual lifting activities associated with the risk metrics calculated.

The server then identifies (630) specific physical locations, in the form of warehouse sector numbers, for example, at which the risk metric illustrates a high risk across multiple workers. The method may then recommend (640) location based changes based on the data underlying the risk metric showing high risk. For example, where the risk metric shows that multiple employees are at increased risk because an object must be lifted from a high location, the platform may recommend lowering a shelf on which objects rest or adding a stool for workers to stand on while lifting. Similarly, if workers consistently rotate their backs excessively while performing a task at a specific location in a warehouse, the platform may recommend adding a conveyor to that sector of the warehouse.

Similarly, the server may identify specific tasks rather than physical locations, that result in increased risks for workers. For example, if the first worker 110 and the second worker 140 both generate increased values of the risk metric when their schedules indicate that they were each performing a specific task. Accordingly, if multiple workers consistently demonstrate increased risk when, for example, unloading trailers, that task may be highlighted as a high risk task, and the platform may recommend a change in the methodology for performing that particular task.

A platform incorporating the method may present this data in a number of ways. For example, it may provide a heatmap illustrating metric values.

Rather than incorporating worker schedules, in some embodiments, the sensors 190 may have an additional module for determining worker location by, for example, incorporating a GPS unit or other geolocation components and processes. Alternatively, the sensors may triangulate the location of workers based on proximity to known landmarks, such as beacons.

The server may further identify (650) specific workers with higher average risk metrics than others in specific areas. In such a scenario, the method may recommend (660) changes specific to that worker, such as corrections to the worker's posture, or it may recommend (670) utilizing that worker in a different location in the warehouse where they would not be placed at risk. For example, where a specific worker is shorter than others and therefore shows an increased risk in a specific location, the platform may recommend reassigning that worker to a different region.

Social motivation and competition may be incorporated into a work environment using the methods described. Accordingly, the wearable device 4010 can be used to encourage motivation towards the goal of reduced injury risk and improved productivity in several embodiments. In some embodiments, feedback may be provided to individual workers relating their performance to the performance of others. This may be in the form of a rank on a leaderboard, for example.

In such an embodiment, a worker wearing the device, can access, through the device or through a related platform, an employee ranking or leaderboard which shows the rank of the worker for a specific metric compared to their peers. For example, a ranking of workers may be provided based on the number of high risk lifts they have performed over a given time period. By seeing their rank, a worker may be motivated to improve their performance, especially if combined with incentives, such as a gift card, points etc.

Alternatively, a worker may be provided with a daily target for a specific metric, which can then be shown on the screen of the device. When the worker achieves the goal, the device may provide a notification to the worker or management. For example, a target for a productivity metric, such as number of lifts, or a goal for a safety metric, such as the number of lifts performed with good biomechanical posture may be created within the systems described.

The platform may further advise on shift changes. In this embodiment, workers who are at increased risk of injury after a certain number of hours of their shift because of fatigue, or other reasons, can be shifted to another task that uses alternate muscles in order to reduce their risk of fatigue induced injuries. In addition, the unloading or loading of a trailer, or other high intensity tasks, can be scheduled to coincide with times of the shift where workers at least fatigued.

Figure 8:
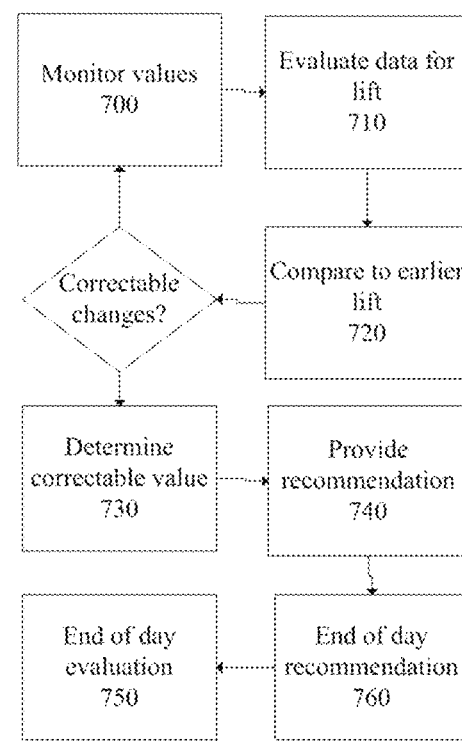
FIG. 8 illustrates an alternate method for generating recommendations.

FIG. 8 illustrates an alternate method for generating recommendations. As shown in the figure, the server monitors (700) the values of the risk metric determined in the method of FIG. 3 across multiple lifts for a specific user. If a specific one of the lifting activities performed by the user demonstrates increased risk as measured by the risk metric, the platform evaluates (710) the data underlying the specific lift being evaluated. The platform then compares (720) each of the underlying metrics to the corresponding metrics determined for earlier lifts performed by the same worker.

If the underlying metrics differ in a specific identifiable way from earlier lifts, the platform determines (730) if the underlying metrics is correctable by the user, and if so, provides a recommendation (740) to address the change. For example, where the platform notes that the horizontal distance between the workers back and wrist has changed, or the user's back angle has shifted, it may recommend correcting the user's posture. The platform may determine that the value has changed by checking each value underlying the metric for each lift against the average value of the corresponding measurement. If there is a significant difference, such as if the value differs by more than a threshold percentage, the platform may recommend a corresponding change.

Further, in some embodiments, if the risk as described by the model is above a threshold, the individual components of the risk models may be analyzed to determine the cause of the underlying risk, and to present recommendations for addressing the high risk level. For example, if the risk metric provides an increased value and the platform determines that the frequency multiplier is abnormally high, recommendations may be provided based on reducing the frequency rates of lifts or having more people perform the job so as to reduce the load on each individual worker.

This recommendation may be provided to a worker as soon as detected by the platform by providing feedback corresponding to the aspect of the worker's posture that should be addressed. For example, where the distance between wrist and back has changed, haptic feedback may be applied to the worker's wrist, while if the back angle has changed, such feedback may be applied to the user's back.

Additional recommendations may be generated by the platform. For example, depending on the values for the variables underlying the risk metric, the platform may recommend bringing a load closer to the worker by removing any barriers or obstacles between the worker and the load, avoiding lifts beginning near the floor, avoiding lifts over shoulder height, reducing the vertical distance between the origin and the destination of a load, reducing a lifting frequency, or allowing for longer recovery periods between lifts. Further, the platform may recommend improving posture by straightening the worker's back and lifting with his legs or turning feet and stepping to move loads rather than having a worker twist his back.

In addition to recommendations, the a platform implementing the method may generate actionable visualizations by summarizing metrics recorded over the course of an evaluation period, or over an extended period of time, by providing charts indicating high risk times of days, weeks, or months, so that specific risks may be identified and addressed. The platform may further identify, for example, a percentage of high risk lifts or total number of high risk lifts performed in a specified period of time.

Such an evaluation may be done in real-time by providing such feedback during a work shift. Alternatively, or in addition, the platform may provide (750) an end of day evaluation. Such an evaluation may, for example, demonstrate worsening posture over the course of the day indicating fatigue. In such a scenario, the platform may provide a recommendation (760) such as a scheduling change or a reorganization of tasks. For example, the platform may recommend lifting heavier objects earlier in a shift.

While the method is described with respect to a risk metric, the method may further be used to monitor productivity across tasks for individual workers. This may be by monitoring, for example, frequency of lifts, or productivity over the course of a shift. For both the methods illustrated in FIGS. 7 and 8, where recommendations are made, the results of those recommendations may be monitored based on the productivity metric as well as the risk metric in order to evaluate whether the recommended change was effective. Accordingly, where a piece of equipment was recommended and implemented in a specific location, the platform may monitor future activity in that location to determine if injury risk has in fact decreased and/or to determine if productivity has in fact increased in that location. This information can be incorporated into future modeling of that particular change.

Metrics relating to productivity of individual workers may be further developed, and productivity based metrics may be utilized to evaluate relationships between fatigue and productivity. Accordingly, the platform may provide estimates of return on investment for individual pieces of equipment that may both reduce injury risk and increase productivity. In some cases, a reduction in injury risk may lower productivity, while a requirement for a worker increasing productivity may increase the risk for that particular worker. The platform described may determine an appropriate balance of increasing a worker's productivity while maintaining the risk metric below a specified threshold.

In some embodiments, fatigue of workers may be evaluated by estimating energy associated with motion of the worker. Fatigue affects risk and is typically incorporated into measurements in the form of lift rate, and in generating an effective weight lifted, as discussed above with respect to step 490. Fatigue may be further evaluated by monitoring average acceleration rates of the wrist and back of the worker over time, including during non-lifting activities, such as inventory checking or manufacturing processes. By detecting reductions in acceleration rates over time, such a method may then identify fatigue and determine potential and kinetic energies expected by a workers body.

The platform described may provide immediate feedback to workers themselves, or it may provide feedback directly to managers, either through on screen notifications at their workstations or through text messages to immediately notify a manager to an increase risk level for an employee. Similarly, the platform may provide rankings for individual workers, or may alert the manager when the workplace as a whole has generated an increased risk profile.

Figure 9:
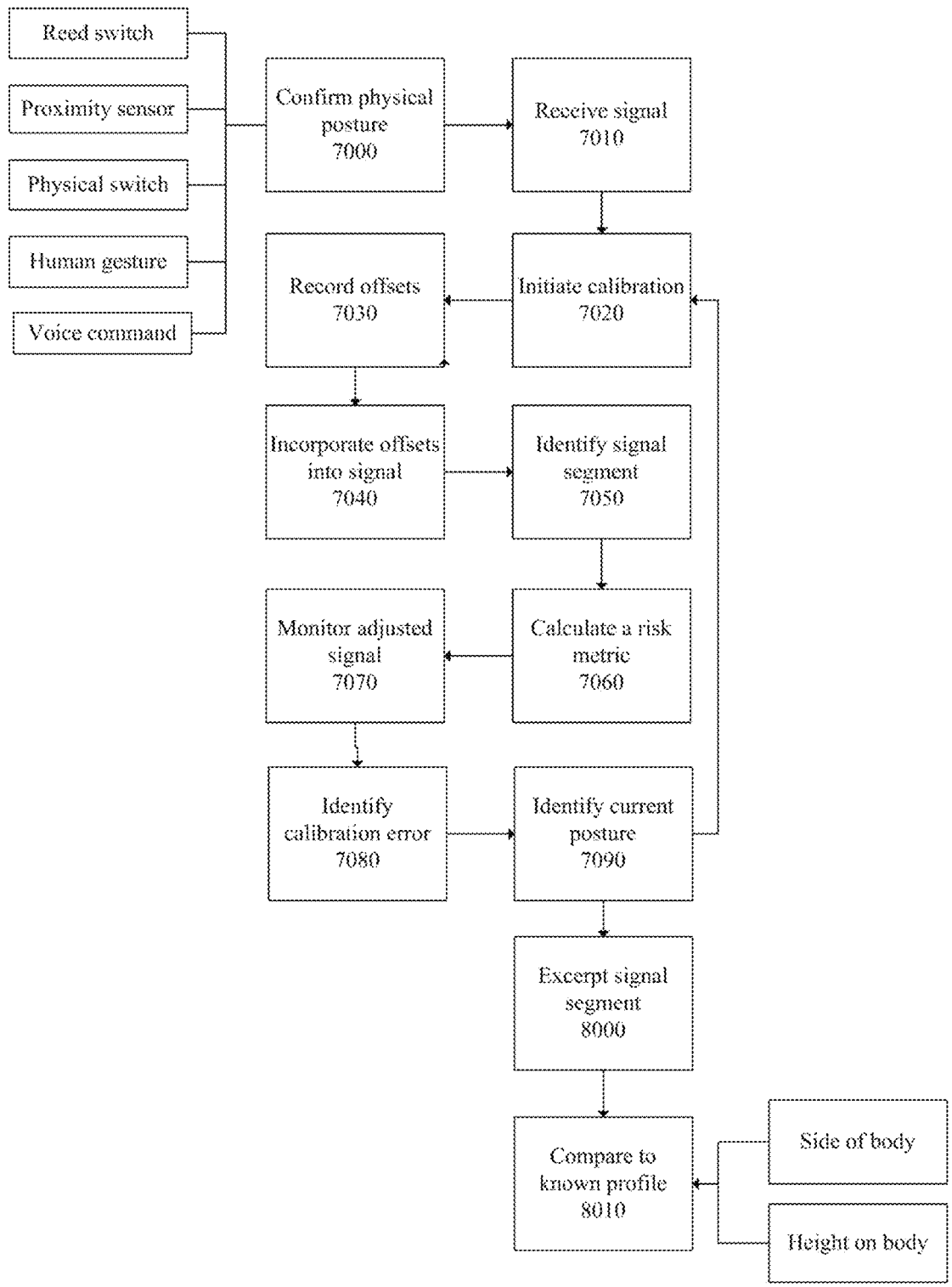
FIG. 9 illustrates a method for calibrating wearable sensors.

FIG. 9 illustrates a method for calibrating wearable sensors 190. Such a method may be implemented using the sensor packaging 2000 shown in FIGS. 2B-2D in order to properly calibrate the sensors 190 prior to beginning the detection of particular activities.

The method initially confirms (7000) that an actual physical posture or movement of a user wearing the wearable device 4010 corresponds to a known physical posture or movement, captures an initial state of all sensors, and begins to receive (7010), at a processor, a first signal from a wearable device 4010, the signal indicative of physical characteristics of the wearable device 4010 over time. For example, the signal may reflect orientation, height, or acceleration information indicative of the location and movement of the wearable device 4010 over time.

The actual physical posture may be, for example, a standardized standing or sitting position. The confirmation of such posture may be by monitoring a clip 2010 on the wearable device 4010 and proceeding with the method upon the closure of the clip. The closure of the clip 2010 may be detected by a switch integrated into the clip, such as a magnetic field sensor or reed switch. In some embodiments, a user may be instructed to assume a particular posture, such as standing up straight, and may then confirm that they have assumed the posture by, for example, gesturing or pushing a button confirming the posture assumed posture. In some embodiments, a user may tap the wearable device 4010, resulting in a spike of acceleration data from the accelerometer 210, in order to indicate that the posture has been assumed. In some embodiments, such confirmation may be a voice command, a gesture, a physical switch, or a proximity sensor.

Alternatively, the method may require the user to assume one of several known postures and instruct a user to either sit straight up or stand straight, and the wearable device 4010 may detect which position has been selected and calibrate accordingly.

The method then initiates (7020) a calibration sequence. The calibration sequence correlates the first signal received from the wearable device 4010 with the known physical posture of the device at that time. Accordingly, the calibration sequence includes recording offsets (7030) for the first signal in a memory, the offsets accounting for any difference between an expected first signal and the physical characteristics actually measured in the first signal.

The offsets recorded may include offsets to be applied to raw data from a 3-axis accelerometer 210, gyroscope 220, magnetometer, or altimeter, or to a fusion of data, such as quaternion data.

Once the offsets are recorded, they are incorporated (7040) into an adjusted first signal, and the adjusted first signal is then used to implement the various methods described elsewhere in this disclosure. Accordingly, once the first signal is adjusted, the method identifies, (7050) in the adjusted first signal, a signal segment corresponding to a physical activity, and calculates (7060) a risk metric from a risk model based on the signal segment corresponding to the physical activity, the risk metric being indicative of high risk physical activity.

Figure 10A:
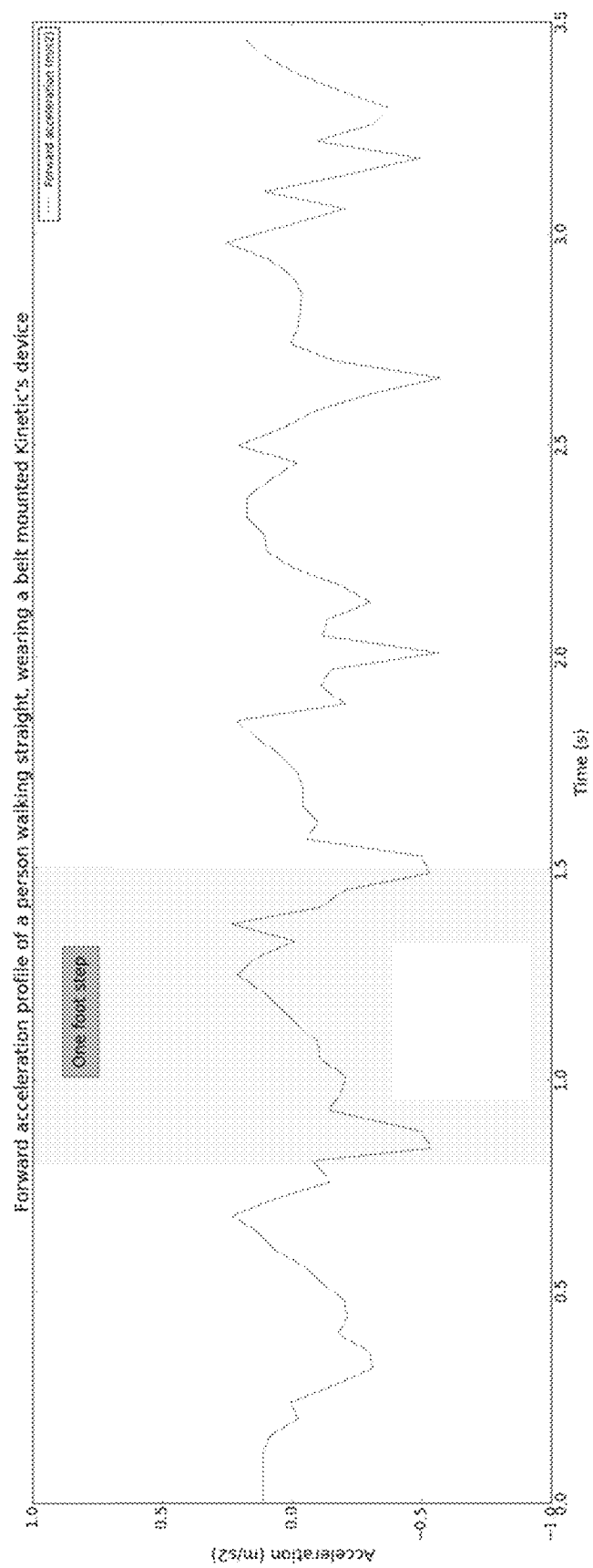
FIGS. 10A-B show acceleration profiles generated by the wearable sensors.
Figure 10B:
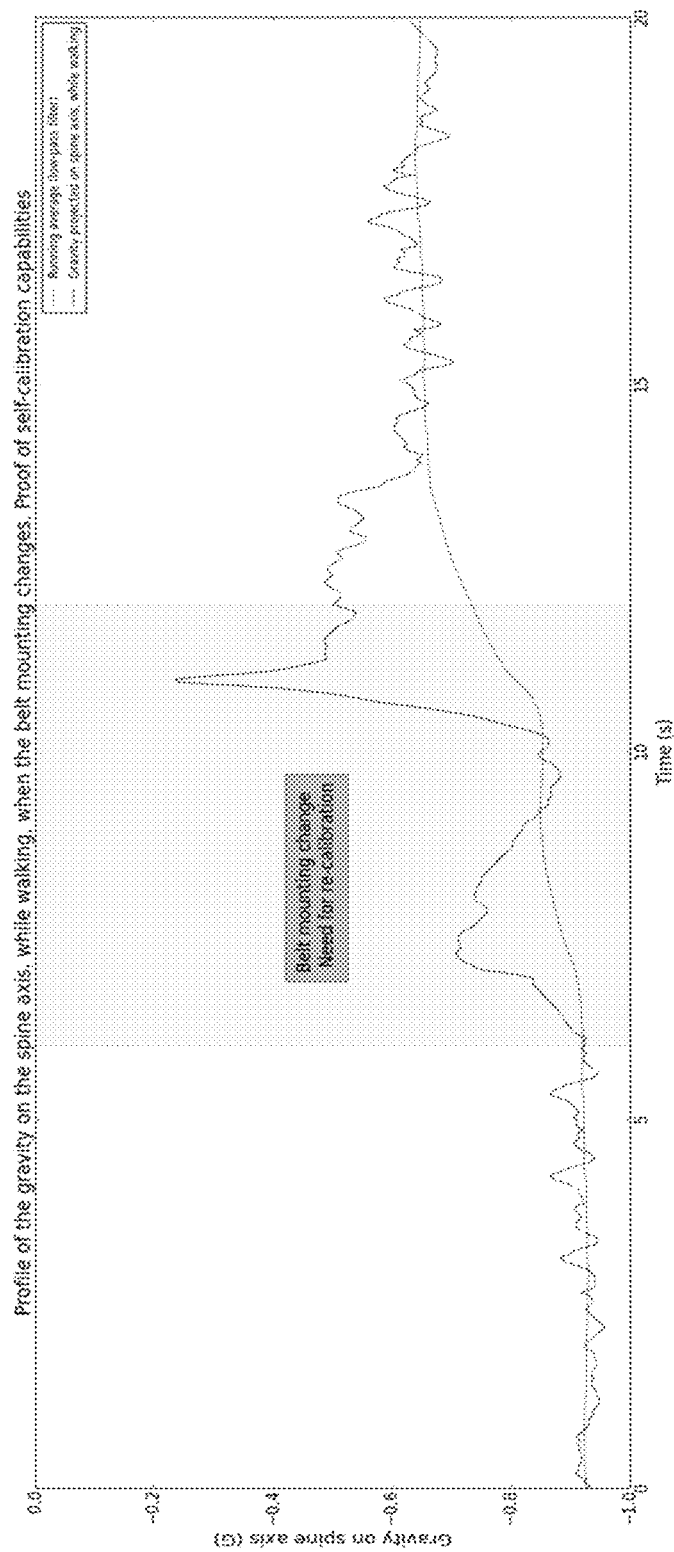

In some embodiments, the method continues to monitor (7070) the adjusted first signal and identifies (7080) a signal segment corresponding to a known category of calibration error. For example, if the wearable device 4010 is knocked and is rotated with respect to the user's belt line or slides along the user's belt, the adjusted first signal may provide data indicating a dangerous motion, when the data really indicates a calibration error based on the new positioning of the wearable device. As one example, FIG. 10A shows an acceleration profile corresponding to a user of the wearable device 4010 walking. FIG. 10B shows that acceleration profile modified by a known category of calibration error, where, for example, the wearable device 4010 is knocked out of alignment while the user is walking.

Accordingly, if such a calibration error is detected, the method may identify (7090) the current actual posture or motion of the user by incorporating the calibration error into its evaluation and reinitiate (at 7020) the calibration sequence. In some embodiments, the calibration sequence is reinitiated at regular intervals, regardless of whether a known category of calibration error is detected, in order to maintain proper calibration.

The identification of the current actual posture or motion of the user (7090) may be, for example, by monitoring the first signal for common known acceleration profiles, such as a worker walking profile shown in FIG. 10A. The method may then implement the calibration sequence while the user is walking by, for example, averaging the movement of the user to determine the appropriate offsets for the device. In other embodiments, the method may observe the user walking to confirm that the segment of the first signal is, indeed, indicative of a calibration error and may then initiate (at 7020) the calibration sequence when the user stops walking, assuming the user remains upright.

Alternatively, once the system is properly calibrated, the method may monitor a moving average of common known acceleration profiles. In such a case, if the moving average moves dramatically, such as that shown in FIG. 10B, the moving average algorithm may either modify the offsets or compensate the algorithms accordingly. Various statistics other than a moving average may be used as well.

In some embodiments, the calibration method may further determine a wearing position or device location of the wearable device 4010 relative to the user. To do so, the method may monitor (7090) common known acceleration profiles, such as the profile of a user walking shown in FIG. 8A, and may excerpt a calibration signal segment (8000) corresponding to a known action, such as a single footstep or a set of footsteps. The method may then compare (8010) the calibration signal segment to expected profiles for that known action based on assumptions that the wearable device 4010 is worn in different positions, such as above or below the pelvic bone or on the left or right hip. In some embodiments, the calibration signal segment may, instead, be compared to the expected profiles and variance of the signal relative to the expected profile may be used to identify wearing positions corresponding to known variances.

Figures 11A, 11B:
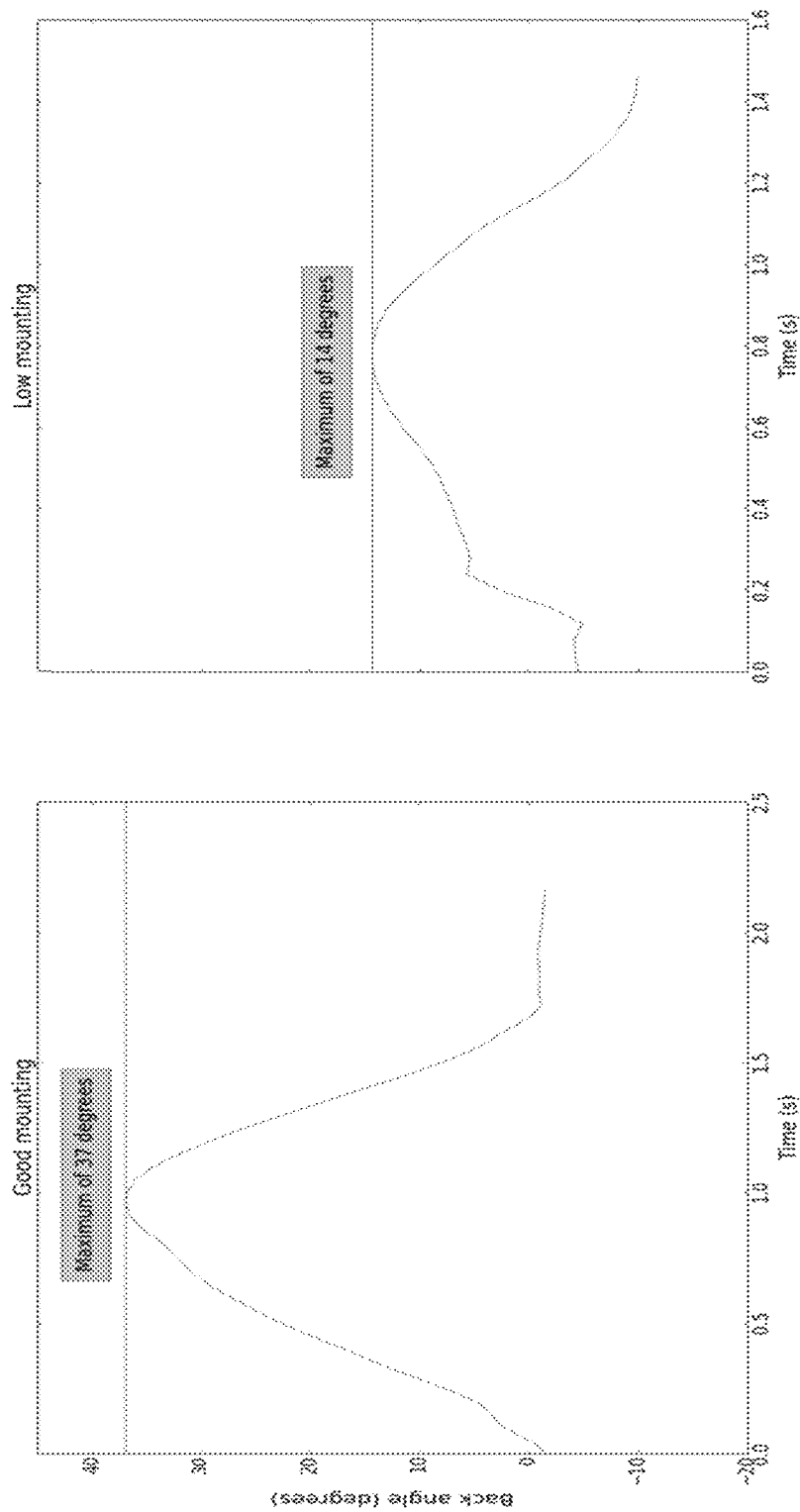
FIGS. 11A-B show rotation profiles generated by the wearable sensors.

For example, when a user bends over, the maximum rotation of the wearable device 4010 will vary depending on whether it is worn higher or lower than expected. FIG. 11A, for example, shows the rotation of a wearable device 4010 against time for a user bending over when the device is properly mounted above a user's hip. As shown, the user's back angle is properly measured to achieve a maximum rotation of 37 degrees. In contrast, FIG. 11B shows the rotation of the wearable device 4010 for the same action when the device is mounted lower on the user's body, showing a maximum rotation of 14 degrees. Accordingly, when the method identifies an improper profile, such as that shown in FIG. 11B, the method may either trigger an alert, instruct the user to correct the mounting position, or it may modify the algorithms or recalibrate the device accordingly.

Figure 12B:
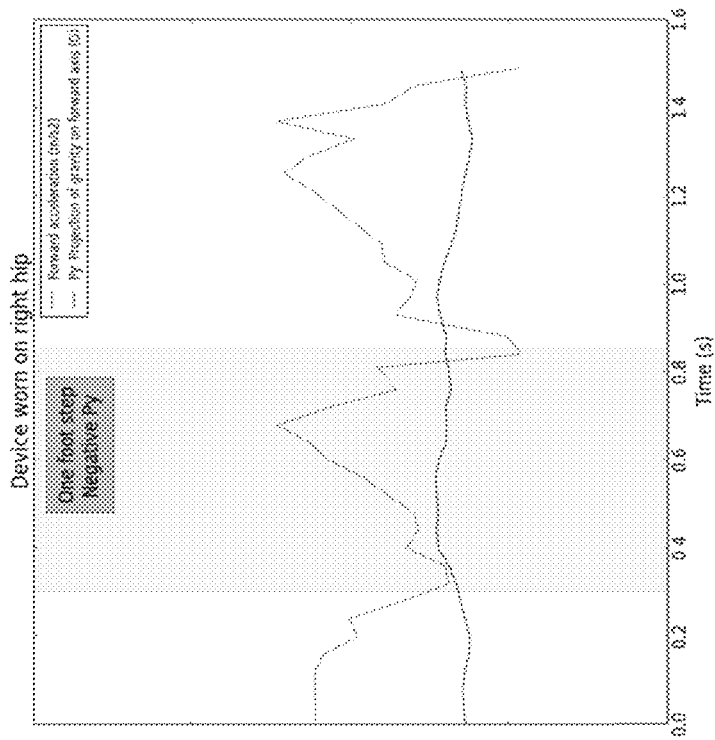
FIGS. 12A-B show acceleration profiles generated by the wearable sensors.
Figure 12A:
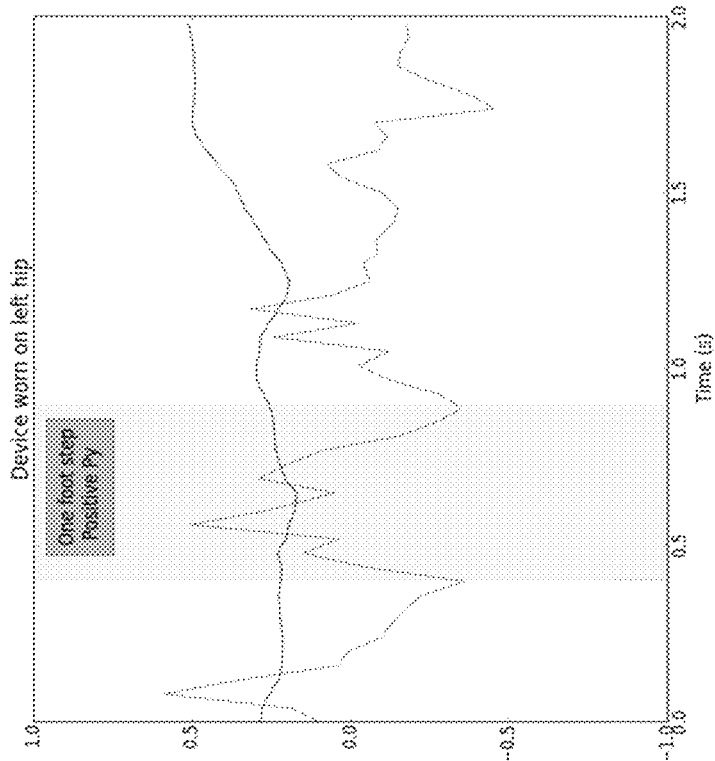

Similarly, an acceleration profile for a known activity will vary depending on wearing position of the wearable device (4010). For example, when a user is walking, the resulting profile will be different if the user wears the device on his left hip, as shown in FIG. 12A, than if the user wears the device on his right hip, as shown in FIG. 12B.

In order to increase the accuracy of the calibration method, a user may be instructed to perform a known action. For example, a user may be instructed to bend their back with or without bending their knees in order to determine the mounting height of the wearable device 4010. The user may also be asked to twist their back in order to determine the maximum rotation of the wearable device 4010 in that context.

Many features of the methods and systems described are enhanced by associating each wearable device 4010 with a specific user. The proper association during ensures accurate and consistent evaluation of risk metrics, and further ensures that measurements are associated with the correct user.

In some embodiments, the device may be assigned to a particular user through a software web interface, using the serial number of the device, the device name, label, or alias, for example. This information is then stored on a web server and communicated to the device. In order to confirm the association, the device may, for example, display the user's name and a unique company label. Every day before work starts, the user picks up their associated device showing his or her name and the unique label number.

In some embodiments, the identification of a particular user may be based on details within the calibration signal segment discussed above. For example, when a user initiates the calibration process, the method may track a user walking for a few steps and then analyze the user's gait in order to identify the particular user.

In some embodiments, the wearable devices 4010 each have RFID readers to read the worker's badge or entry card and associate themselves to that worker. This may be done on a daily basis, such that each day a user may pick up one of several available wearable devices 4010 and associate that device with their own profile. Alternatively, the association may be manually created by a user entering their name, employee ID or other unique identifying feature at a user interface, so the device can associate the data to that specific worker. In some embodiments, this association may allow the user to use the wearable device 4010 as a key to authorize access to particular locations within a facility or specific equipment.

In some embodiments, the data and metrics collected and computed by the systems and methods provided can be combined with other available data, both individual to the worker as well as aggregated across the worker, job type, facility, company, or industry. Typical data collection studies might involve:

Identifying industries and jobs involved with musculo-skeletal injury risk;

Examining a specified company's injuries records; and

Collecting worker motion sensor data by means of the invented device.

Once these three steps are completed, a study operator could assess current state of the art ergonomic models with respect to their predictive power and limitations while designing dynamic, sensor-based, prediction models.

Most currently used ergonomic models rely on static data points to analyze motion, are based on data collected for only a few days, if not hours, per employee, and per job type, and focus on a very specific activity and do not encompass tasks' true complexity. By using the wearable device 4010 described, continuous sensor measurements over longer time periods and across different industries and job types, as well as more granular worker-specific data (such as past injuries, days off work, incident rates, behavior observation, age, gender, and medication taken), correlations between specific repetitive motions and injury factors may be examined and more accurate and precise predictive models may be developed.

The results of such studies may be used to increase the predictability of past data, and may increase the quality of, for example, actuarial evaluations of workers for the purpose of insurance rates. Separately, data may be used to reorganize workplaces for increased safety and efficiency and various safety requirements may be associated with tasks based on particular injury risks uncovered in the data. In some embodiments, users may volunteer to be monitored using the wearable device 4010 in exchange for a reduction in their own insurance rate, and the data acquired may be used to more granularly adjust the rate or penalize or reward the user.

Figure 13:
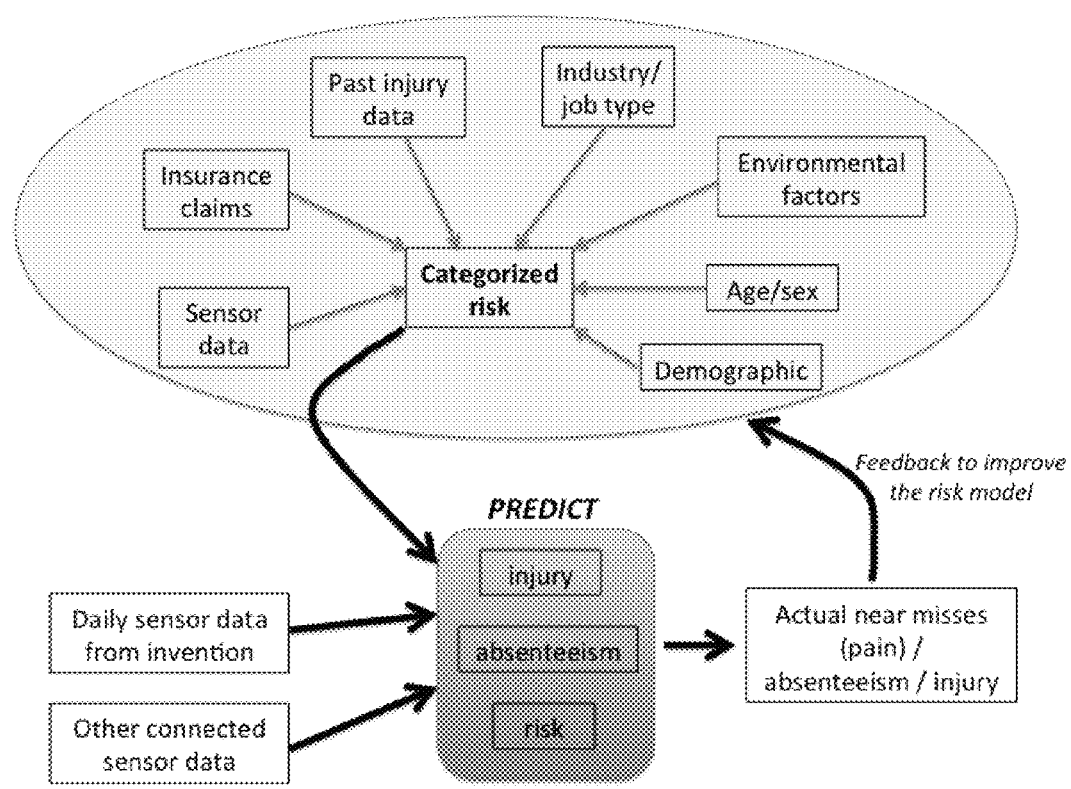
FIG. 13 shows a model for using the methods provided for evaluating risks.

Any model based on the dynamic data described may then generate data that feeds back into the model. As shown in FIG. 13, various categorized risks associate with a user, including risks based on the sensor data generated and evaluated using the methods described, may be used to predict injury, absenteeism, and other risk. Over time, the model may then be informed of actual injuries, etc., which may then refine the model.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" and like terms encompass all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwithstanding that insubstantial modifications of the invention, not presently foreseen, may nonetheless represent equivalents thereto.

What is claimed is:

1. A computer-based method for identifying a physical activity in a calibrated signal from a wearable device comprising:
   determining that an actual physical posture of a user wearing the wearable device corresponds to a known physical posture;
   receiving, at a processor, a first signal from the wearable device generated from dynamic activity of the wearable device over time;
   initiating a calibration sequence, the calibration sequence including excerpting a calibration window of the first signal and recording, at a memory, offsets in the first signal relative to an expected value of the first signal corresponding to the known physical posture;
   incorporating the offsets into an adjusted first signal;
   identifying, in a portion of the adjusted first signal following the calibration window, a signal segment corresponding to a physical activity; and
   identifying the physical activity based on the signal segment.

2. The computer-based method of claim 1, wherein the physical activity is a lifting activity performed by the user of the wearable device and the method further comprises calculating a risk metric from a risk model based on the signal segment, the risk metric being indicative of high risk physical activity.

3. The computer-based method of claim 2, wherein the identifying of the signal segment is by identifying an initiation time for the lifting activity performed by the wearer of the wearable device, and excerpting the signal segment corresponding to a time period after the initiation time.

4. The computer-based method of claim 3, further comprising determining a conclusion time for the lifting activity and repeating the method to identify a plurality of lifting activities over an evaluation period.

5. The computer-based method of claim 1, wherein the determining that an actual physical posture of the user wearing the wearable device corresponds to a known physical posture comprises:
   providing the user with the wearable device;
   monitoring a clip of the wearable device; and
   confirming the closure of the clip,
   wherein the device is applied to a user while the user is in a known physical posture.

6. The computer-based method of claim 5, wherein the confirming of the closure of the clip is by registering the closure with a magnetic field sensor.

7. The computer-based method of claim 1, wherein the determining that an actual physical posture of a user wearing the wearable device corresponds to a known physical posture comprises recording an indication by a user that the user is in a predetermined physical posture or by instructing the user to conform to an initial posture and indicate the assumption of that initial posture.

8. The computer-based method of claim 1, further comprising:
   identifying, in the adjusted first signal, a signal segment corresponding to a known category of calibration error;
   identifying, in the adjusted first signal, a signal segment corresponding to a known activity incorporating the known category of calibration error; and
   initiating the calibration sequence.

9. The computer-based method of claim 8, wherein, the known category of calibration error is a rotated device and the known activity is the user walking.

10. The computer-based method of claim 1, further comprising identifying, in the first signal, a calibration signal segment corresponding to an expected pattern for a calibration activity; and
    identifying a device location relative to the user based on a variance between the calibration signal segment and the expected pattern.

11. The computer-based method of claim 10, wherein the device location is a side of the body or a height relative to a user's hips.

12. The computer-based method of claim 1, wherein:
    the identifying of the signal segment comprises identifying, in the adjusted first signal, an initiation time for a physical activity performed by the user wearing the wearable device and wherein the signal segment is a segment of the adjusted first signal for a time period following the initiation time for the physical activity, the time period being a time period during the physical activity;
    wherein the method further comprises:
      excerpting the signal segment;
      calculating measurements of the user for the time period during the physical activity from the signal segment; and
      calculating a risk metric from a risk model based on the measurements of the wearer for the time period during the physical activity, the risk metric being indicative of high risk physical activity.

13. The computer-based method of claim 12 further comprising determining a conclusion time for the physical activity and repeating the identifying of the signal segment to identify a plurality of physical activities over an evaluation period, wherein the excerpted signal segment is for the time period following the initiation time and prior to the conclusion time for the corresponding physical activity.

14. The computer-based method of claim 13 further comprising calculating a cumulative risk metric indicative of high risk physical activity over time and outputting feedback indicative of a high risk when the cumulative risk metric is above a threshold level.

15. The computer-based method of claim 12 wherein the wearable device is mounted at the user's hip, and the measurements calculated include measurements of the user's back inferred from movement of the user's hip detected by the wearable device.

16. The computer based method of claim 15 wherein the movement of the user's hip is detected by an accelerometer, a gyroscope, and an altimeter.

17. The computer-based method of claim 12 wherein the physical activity is the user jumping off of a raised surface, and wherein the identification of the initiation time of the signal segment is by observing acceleration in the vertical direction and a change in height.

18. The computer-based method of claim 12 wherein the physical activity is a user falling, and wherein the identification of the initiation time of the signal segment is by observing acceleration and angular velocity.

19. The computer-based method of claim 12 wherein the wearable device has a communication interface for transmitting a wireless signal comprising the measurements of the wearer for the time period during the physical activity and an identification of the wearer, and wherein a second wearable device has a communication interface for receiving the wireless signal, the method further comprising:
   transmitting, by the wearable device, the wireless signal to the second wearable device, and
   transmitting, by the second wearable device, the wireless signal to a server.

20. The computer-based method of claim 1, wherein the determining that an actual physical posture of the user corresponds to the known physical posture is based on identifying, in the first signal, a calibration signal segment corresponding to an expected pattern for a calibration activity.

21. The computer-based method of claim 20, wherein the calibration activity is the user walking.

22. The computer-based method of claim 21 further comprising:
   identifying, in the adjusted first signal, a signal segment corresponding to the user walking, and
   initiating an additional calibration sequence.

23. The computer-based method of claim 14, wherein the outputting of feedback indicative of the high risk occurs only when the cumulative risk metric and the risk metric are each indicative of high risk physical activity.

\* \* \* \* \*